US008448327B2

(12) United States Patent
Tonami

(10) Patent No.: US 8,448,327 B2
(45) Date of Patent: May 28, 2013

(54) METHOD OF MANUFACTURING RADIATION TOMOGRAPHY APPARATUS

(75) Inventor: Hiromichi Tonami, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 365 days.

(21) Appl. No.: 12/991,205

(22) PCT Filed: May 12, 2008

(86) PCT No.: PCT/JP2008/058732
§ 371 (c)(1),
(2), (4) Date: Nov. 5, 2010

(87) PCT Pub. No.: WO2009/139039
PCT Pub. Date: Nov. 19, 2009

(65) Prior Publication Data
US 2011/0056063 A1    Mar. 10, 2011

(51) Int. Cl.
*G01R 3/00* (2006.01)
(52) U.S. Cl.
USPC .............................. 29/595; 29/592.1; 29/593
(58) Field of Classification Search
USPC ........................................ 29/592.1, 593, 595
See application file for complete search history.

(56) References Cited

U.S. PATENT DOCUMENTS

| 4,625,117 | A  | * | 11/1986 | Hayakawa et al. ......... 250/385.1 |
| 5,030,830 | A  | * | 7/1991  | Okada ........................ 250/361 R |
| 6,087,663 | A  | * | 7/2000  | Moisan et al. ................ 250/367 |
| 6,807,248 | B2 | * | 10/2004 | Mihara et al. .................... 378/10 |
| 7,087,905 | B2 | * | 8/2006  | Murayama et al. ........... 250/367 |
| 7,142,634 | B2 | * | 11/2006 | Engler et al. .................... 378/65 |
| 8,274,055 | B2 | * | 9/2012  | Ohi et al. ................. 250/363.07 |

FOREIGN PATENT DOCUMENTS

JP         2004-279057 A    10/2004

* cited by examiner

Primary Examiner — Carl Arbes
(74) Attorney, Agent, or Firm — Cheng Law Group, PLLC

(57) ABSTRACT

A method of manufacturing radiation tomography apparatus according to this invention includes a first spacer joining step of joining a spacer to a radiation detector, and a second spacer joining step of joining both the radiation detectors to each other via the spacer such that clearance between adjacent scintillators corresponds to integral multiples of an arrangement pitch of scintillation counter crystal. Accordingly, the scintillators provided in the radiation tomography apparatus of this invention are arranged more regularly, which achieves enhanced spatial resolution of the radiation tomography apparatus.

20 Claims, 14 Drawing Sheets

Fig.6
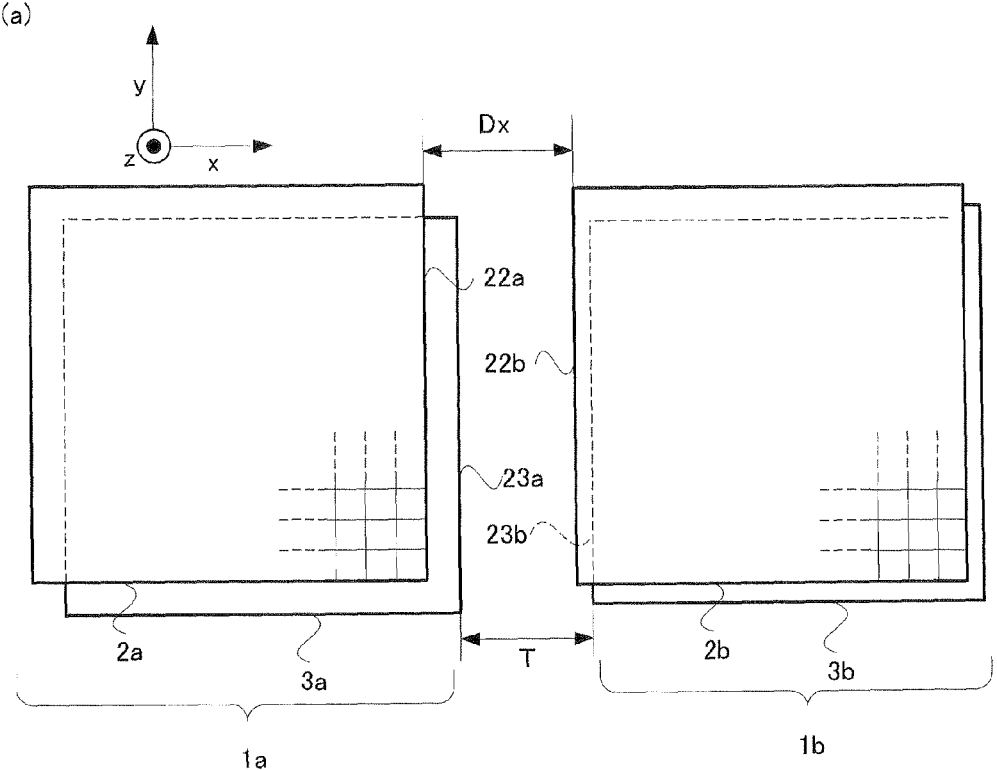
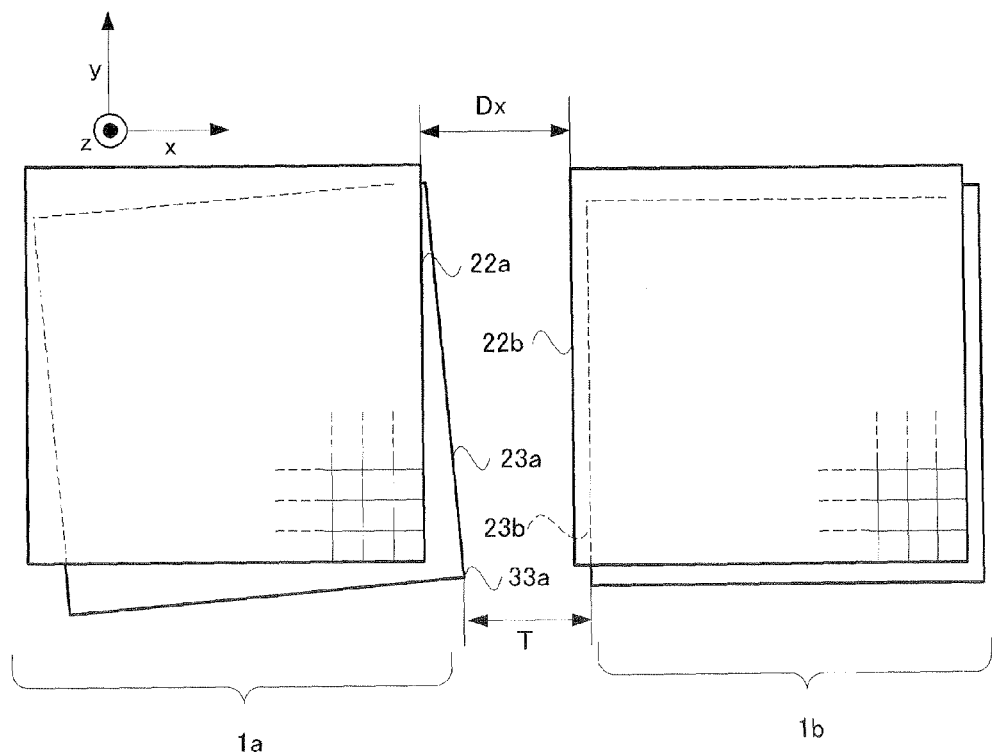

Fig. 7
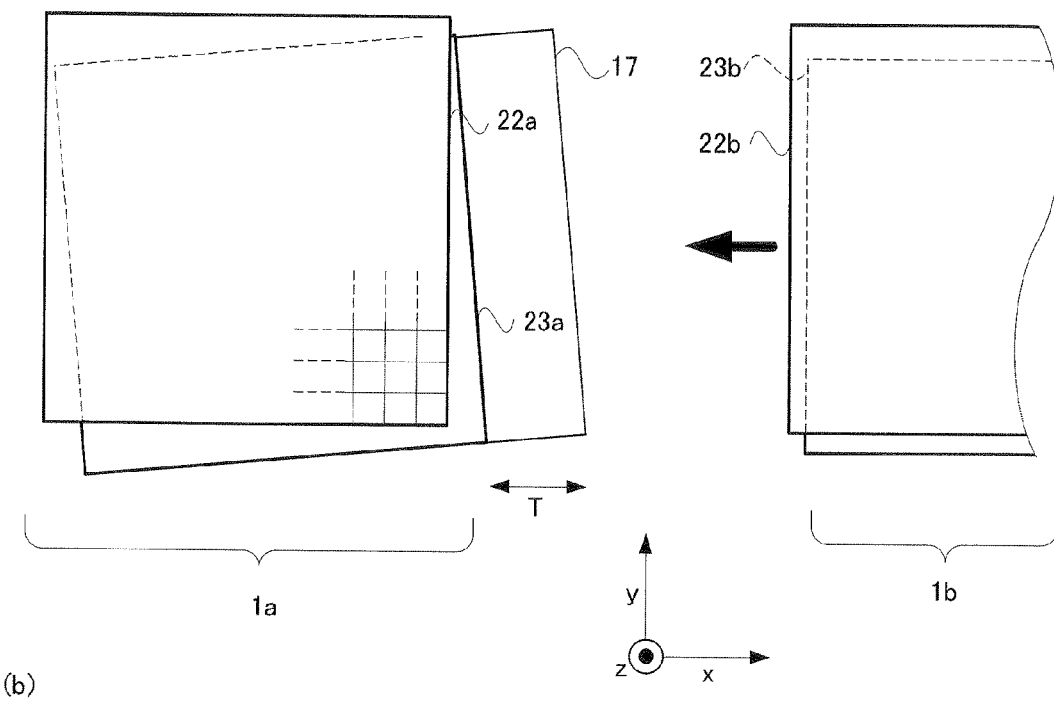
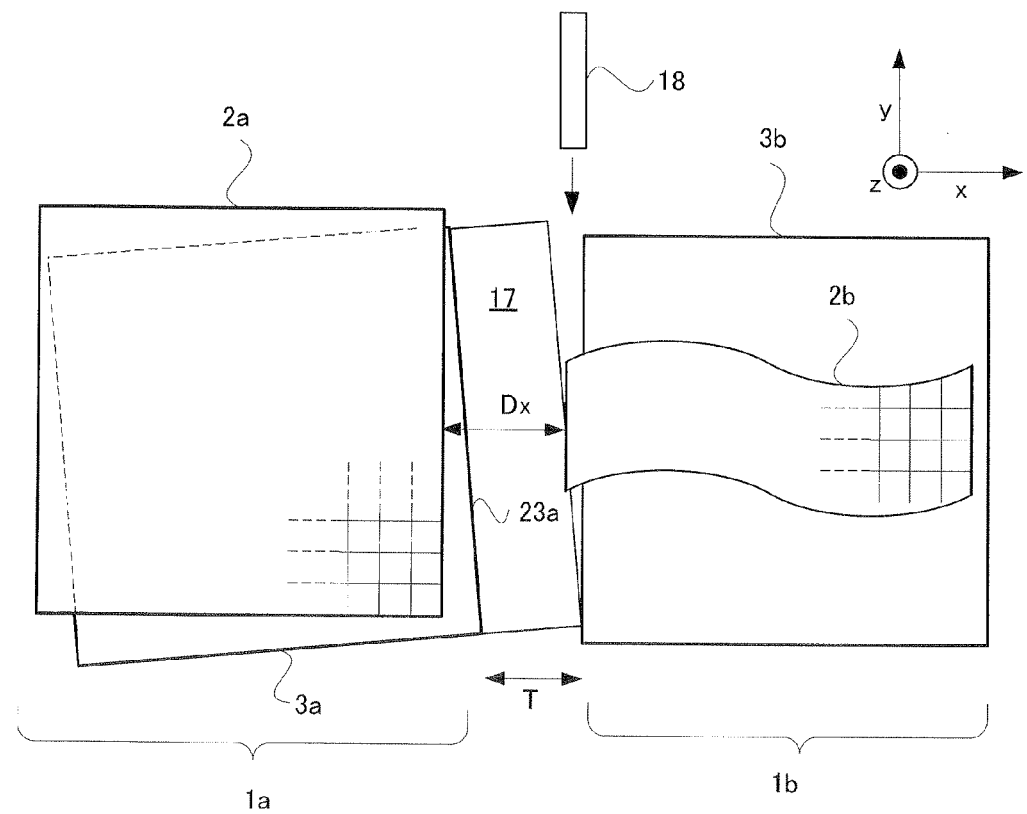

Fig.10
(a)
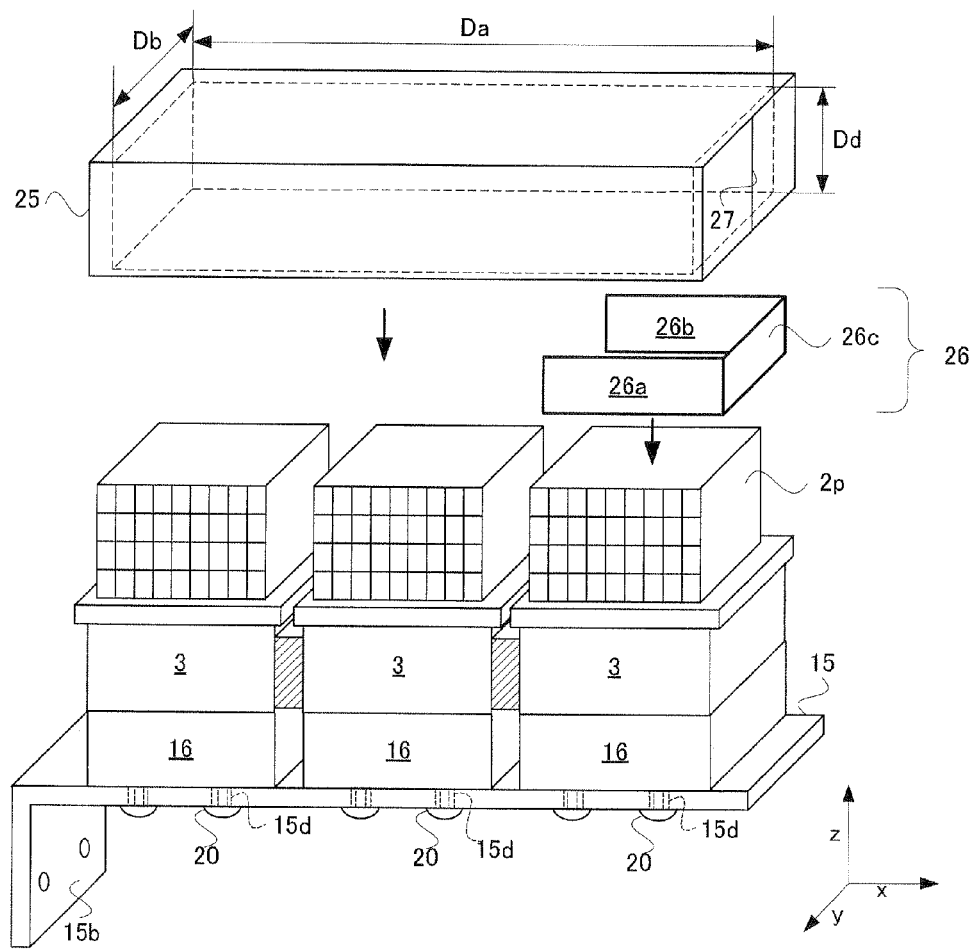
(b)
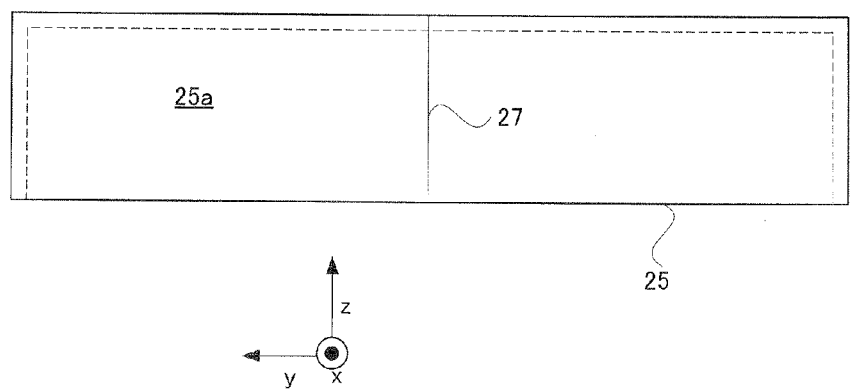

Fig. 17
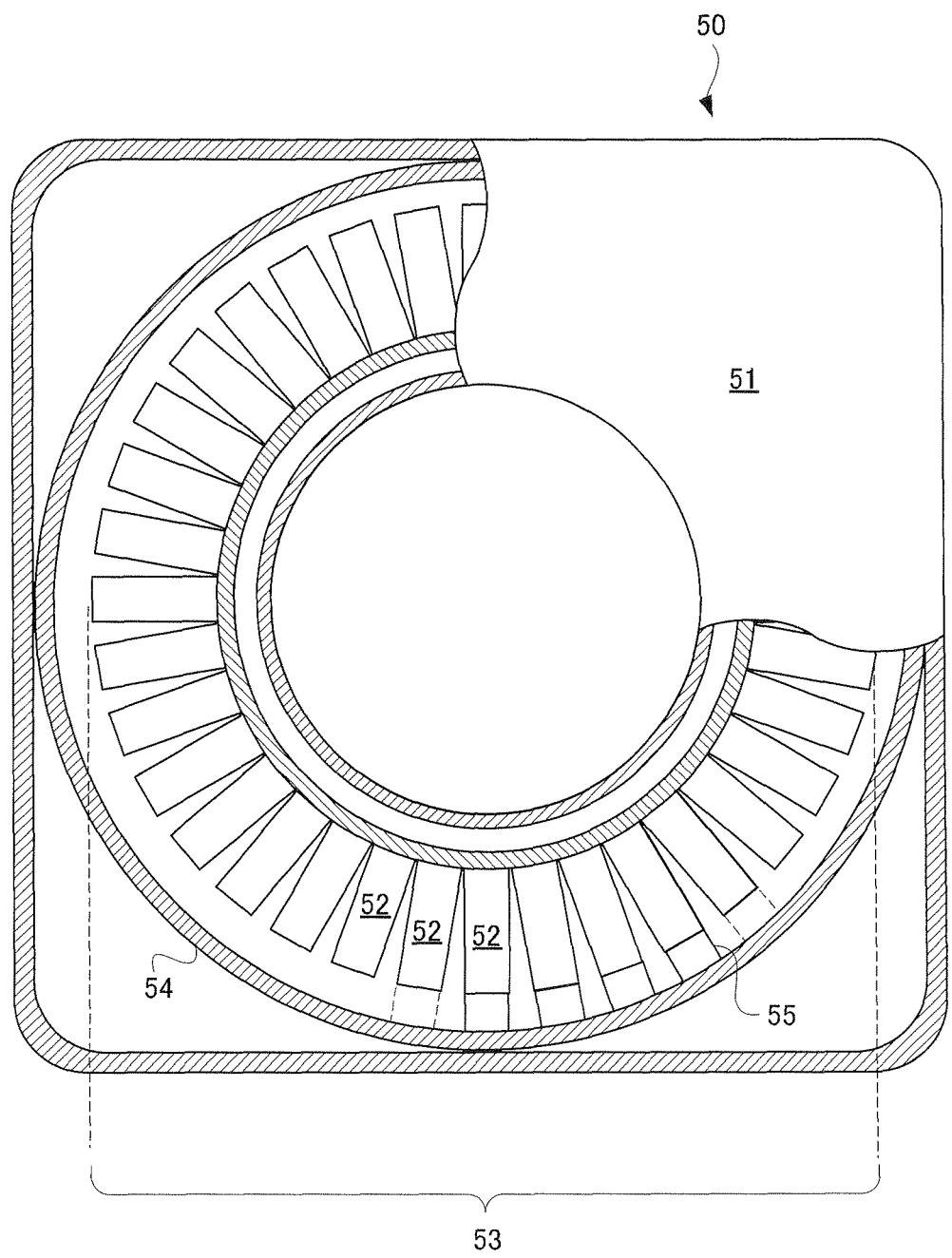
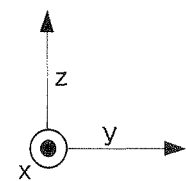

METHOD OF MANUFACTURING RADIATION TOMOGRAPHY APPARATUS

TECHNICAL FIELD

This invention relates to tomography apparatus that images radiation. Particularly, this invention relates to tomography apparatus provided with a detector ring having block radiation detectors arranged in a ring shape.

BACKGROUND ART

In medical fields, emission computed tomography (ECT: Emission Computed Tomography) apparatus is used that detects radiation (such as gamma rays) emitted from radiopharmaceutical that is administered to a subject and is localized to a site of interest for obtaining sectional images of the site of interest in the subject showing radiopharmaceutical distributions. Typical ECT apparatus includes, for example, a PET (Positron Emission Tomography) device and an SPECT (Single Photon Emission Computed Tomography) device.

A PET device will be described by way of example. The PET device has a detector ring with block radiation detectors arranged annularly. The detector ring is provided for surrounding a subject, and allows detection of radiation that is transmitted through the subject.

Such radiation detector arranged in the detector ring of the PET device is often equipped that allows position discrimination in a depth direction of a scintillator provided in the radiation detector for improved resolution. First, description will be given of a configuration of a conventional PET device. As shown in FIG. 17, a conventional PET device 50 includes a gantry 51 with an introducing hole that introduces a subject, a detector ring 53 having block radiation detectors 52 for detecting radiation that are arranged inside the gantry 51 so as to surround the introducing hole, and a support member 54 provided so as to surround the detector ring 53. Each of the radiation detectors 52 has a bleeder unit 55 with a bleeder circuit in a position between the support member 54 and thereof for connecting the support member 54 and the radiation detector 52. The bleeder unit 55 is coupled to a light detector 62, mentioned later, in the radiation detector 52.

Next, description will be given of a construction of the radiation detector 52. As shown in FIG. 16, the conventional radiation detector 52 includes a scintillator 61 that converts radiation into fluorescence, and a photomultiplier tube (hereinafter referred to as a light detector) 62 that detects fluorescence. The scintillator 61 has scintillation counter crystals 63 of rectangular solid that are arranged in a two-dimensional array. The light detector 62 allows discrimination about which scintillation counter crystal 63 emits fluorescence. That is, the radiation detector 52 may discriminate an incidence position of radiation in the scintillator 61. A light guide 64 is provided between the scintillator 61 and the light detector 62 for receiving fluorescence.

Here in the PET device 50, the radiation detectors 52 in the detector ring 53 have to be arranged precisely. The PET device 50 acquires a sectional image based on an incidence direction of radiation. Accordingly, when deviation occurs in arrangement of the radiation detectors 52 in the detector ring 53, the deviation also influences the sectional image acquired with the PET device 50. Specifically, where the radiation detectors 52 in the detector ring 53 are not positioned as they are by an original setting, the incidence position of radiation determined with the detector ring 53 deviates from an actual incidence position thereof even when localization of radiopharmaceutical in the subject is identified from data that is outputted from the detector ring 53. Thus, the conventional PET device 50 has a configuration in which the support member 54 is divided into split sections, and the radiation detectors are loaded therein in order that the radiation detectors 52 are regularly arranged to the extent possible (see, for example, Patent Literature 1.)

[Patent Literature 1]
Japanese Patent Publication No. 2004-279057

DISCLOSURE OF THE INVENTION

Problem to be Solved by the Invention

However, the conventional radiation tomography apparatus has the following drawbacks. That is, according to the conventional configuration, when the radiation detectors 52 are arranged, positioning thereof is performed with reference to the bleeder unit 55. Taking into consideration that, in the radiation detector 52, the incidence position of radiation is identified by discrimination about which scintillation counter crystal 63 emits fluorescence, not the bleeder unit 55 but the scintillator 61 of the elements in the detector ring 53 needs to be arranged regularly. The light detector 62 having the radiation detectors 52 is coupled to the support member 54 via the bleeder unit 55. Consequently, the light detector 62 and the bleeder unit 55 must not deviate in its coupling position.

In addition, according to the conventional radiation tomography apparatus, the scintillator 61 constituting the radiation detector 52 and the light detector 62 must not deviate in its coupling position. Although the light detectors 62 are regularly arranged in the detector ring 53, where the light detector 62 and the scintillator 61 deviate in its coupling position in each of the radiation detectors 52, arrangement of the scintillators 61 will deviate accordingly. According to the foregoing configuration as noted above, upon arrangement of the radiation detectors 52 in the detector ring 53, each of the adjacent scintillators 61 is not ensured to be arranged regularly in the radiation detector 52, since the radiation detector 52 is not positioned with reference to the scintillator 61.

On the other hand, however, when the scintillator 61 is accurately coupled to the light detector 62, the scintillator 61 and the support member 54 are supported on the light detector 62 and the bleeder unit 55, which leads to further deviation in the coupling position of each member. That is, it is not easy to form the detector ring 53 of the conventional configuration while the scintillators 61 are arranged regularly.

In other words, according to the conventional configuration, even when the scintillators 61 are formed with high accuracy, the arrangement of the scintillators 61 deviates when seen the detector ring 53 in its entirety. As a result, high position discrimination function of radiation in the single radiation detector 52 is useless without being efficiently employed in the PET device.

This invention has been made regarding the state of the art noted above, and its object is to provide radiation tomography apparatus having higher spatial resolution by suppressing deviation in arrangement of scintillators and manufacturing a detector ring having the scintillators arranged regularly upon arranging radiation detectors for forming the detector ring.

Means for Solving the Problem

This invention is constituted as stated below to achieve the above object. A method of manufacturing radiation tomography apparatus according to this invention includes an annular detector ring, the detector ring having detector arrays in a ring shape with each of radiation detectors arranged in a first direction in which a scintillator provided with scintillation counter crystal layers that is formed of scintillation counter crystals that convert radiation into fluorescence are arranged two-dimensionally in the first direction and a second direction as vertical and horizontal directions, a light guide that receives fluorescence, and a light detector that detects fluorescence are laminated in a height direction. The method comprises a preliminary arranging step of arranging a first radiation detector and a second radiation detector in the first direction and selects a spacer such that clearance in the first direction between a first scintillator provided in the first radiation detector and a second scintillator provided in the second radiation detector corresponds to integral multiples of an arrangement pitch of the scintillation counter crystal in the first direction, a first spacer joining step of joining the spacer so as to cover a side surface of a first light detector provided in the first radiation detector that faces the first direction thereof, a second spacer joining step of arranging the first radiation detector and the second radiation detector again in the first direction to align both radiation detectors in the second direction such that the first scintillator is same as the second scintillator in position in the second direction, and joining the spacer to a side surface of a second light detector provided in the second radiation detector to manufacture the detector array extending in the first direction, and a detector ring forming step of forming the detector ring by arranging the detector arrays annularly.

[Effect]

According to this invention, the radiation tomography apparatus may be manufactured that suppresses deviation in arrangement of the scintillators and has the detector ring with the scintillators being arranged regularly. With the configuration of this invention, upon coupling of the first radiation detector and the second radiation detector in series, the spacer is selected such that the clearance in the first direction between the first scintillator provided in the first radiation detector and the second scintillator provided in the second radiation detector corresponds to integral multiples of the arrangement pitch of the scintillation counter crystal in the first direction. Both radiation detectors are coupled via the spacer to manufacture the detector array.

Considering above, the scintillation counter crystals of the detector array have a unified position throughout the detector array so as to correspond to the integral multiples of the arrangement pitch of the scintillation counter crystal regardless of the scintillator to which the scintillator crystal belongs. The scintillation counter crystals are regularly arranged over two or more scintillators that constitute the detector array. In other words, according to this invention, the radiation detector that forms the detector arrays is positioned with reference to the scintillator. In this way, high position discrimination function of the scintillators in which the scintillation counter crystals are arranged with higher accuracy is still efficiently employed after the scintillators constitute the detector ring. Consequently, the radiation tomography apparatus manufactured in accordance with the method of manufacturing the radiation tomography apparatus of this invention fully utilizes accuracy in arrangement of the scintillation counter crystals in the scintillators, thereby having higher spatial resolution.

Moreover, subsequent to the first spacer joining step, there may further be included a shim placing step of placing a shim for adjusting an opposite angle of the first scintillator and the second scintillator between the one side surface of the second light detector and the spacer.

[Effect]

According to the foregoing configuration, even when the light detector is tortuously coupled to the scintillator or has a trapezoidal shape in the radiation detector to be arranged, side surfaces of the first scintillator and the second scintillator opposite to each other may be parallel. In this invention, both radiation detectors are coupled via the light detectors provided therein. Even when the side surfaces of both light detectors are not parallel to each other, the foregoing configuration may ensures parallel of both scintillators to each other, since the shim placing step is included that places the shim for adjusting the opposite angle of both scintillators.

Moreover, in the second spacer joining step, the shim may also be joined to the one side surface of the second light detector and the spacer while the one side surface of the second light detector is joined to the spacer.

[Effect]

According to the foregoing construction, both light detectors may be coupled to each other not only via the spacer but also via the shim. With the foregoing configuration, it is not necessary to pull out the shim from the coupling portion of the spacer and the second light detector. Consequently, the second spacer joining step is simpler. In addition, the spacer is coupled to the second light detector via the shim. Accordingly, the coupling portion of the spacer and the second light detector has a wider surface. As a result, both radiation detectors are to be coupled more firmly.

It is more preferable that the foregoing detector ring forming step includes a detector unit manufacturing step of manufacturing a detector unit by fixing the radiation detector that constitutes the detector array on a support tool that extends in the first direction, a cover attaching step of attaching a cover for covering an upper surface of the scintillators of the detector unit, a detector unit placing step of placing the detector unit on a ring-shaped bottom plate in the first direction such that the scintillators are directed toward inside of the bottom plate, thereby forming a circular ring with the detector units being arranged in a ring shape, an alignment jig placing step of placing a columnar alignment jig inside the circular ring having contact surfaces that face to each of the covers provided in the detector unit, and a detector unit fixing step of fixing the detector unit on the bottom plate by contacting the cover provided in the detector unit to the contact surface to determine a position of the detector unit with respect to the bottom plate.

[Effect]

According to the foregoing configuration, the position of the detector unit with respect to the bottom plate is determined with reference to the alignment jig. Specifically, the position of the detector unit with respect to the bottom plate is to be determined by contacting the cover that covers the scintillator to the contact surface of the alignment jig. As noted above, the detector unit is positioned with reference to the scintillator also in the detector ring forming step. In addition, the scintillator is covered with the cover, which prevents the scintillator from directly contacting to the contact surface of the alignment jig. Therefore, the scintillator may be prevented from being damaged during the detector unit fixing step.

In the foregoing detector unit fixing step, the alignment jig has a first mark that indicates a position of the detector unit whereas the cover has a second mark that indicates a position of the detector unit in the second direction. It is more desirable to determine the detector unit with respect to the bottom plate with reference to the first mark and the second mark.

[Effect]

According to the foregoing configuration, the position may be determined more accurately of the detector unit with respect to the bottom plate. The second mark given to the cover indicates the position of the detector unit in the second direction. Consequently, the detector unit may properly be arranged upon determining of the position of the detector unit with respect to the bottom plate based on the first mark given to the alignment jig and the second mark given to the cover.

Moreover, the foregoing first and second marks are desirably linear marks.

[Effect]

According to the foregoing configuration, the position may be determined more accurately of the detector unit with respect to the bottom plate. Both marks are linear. Consequently, upon determining of the position of the detector unit with respect to the bottom plate with reference to the first mark given to the alignment jig and the second mark given to the cover, the detector unit may regularly be arranged by merely adjusting the position of the detector unit as to conform both marks.

Moreover, radiation tomography apparatus manufactured with the foregoing method of manufacturing the radiation tomography apparatus may include a shim provided between the first and second radiation detectors that form the detector array.

[Effect]

With the foregoing configuration, the radiation tomography apparatus may be provided having the radiation detectors coupled more firmly. In addition, the radiation detectors adjacent to each other are coupled via the shim and the spacer. Accordingly, the coupling portion of the radiation detectors adjacent to each other has a wider surface. As a result, both radiation detectors are to be coupled more firmly, which may realize provision of more rugged radiation tomography apparatus.

Effect of the Invention

According to this invention, provision may be made of radiation tomography apparatus having higher spatial resolution. The scintillators provided in the radiation tomography apparatus of this invention are arranged more regularly. That is because the detector ring is manufactured by adjusting the position of each member that supports the scintillator with reference to the position of the scintillator. The detector ring has the detector unit with the radiation detectors being arranged in series in the first direction. Here, the positions of two or more scintillators of the detector unit are regular. In other words, the scintillation counter crystals that form the detector unit are arranged regularly over two or more scintillators that form the detector array, since clearance of each scintillator corresponds to integral multiples of the arrangement pitch of the scintillation counter crystal. In addition, the detector ring is formed through annularly arranging of the detector units. The position of the detector unit is also determined with reference to the scintillator. That is because the detector unit is positioned with respect to the bottom plate by contacting the alignment jig placed inside the circular ring to the cover that covers the scintillator. As noted above, this invention may arrange the scintillators more regularly, which results in provision of radiation tomography apparatus having higher spatial resolution.

BRIEF DESCRIPTION OF THE DRAWINGS

FIG. 6 is a plan view showing a preliminary arranging step according to Embodiment 1.

FIG. 7 is a plan view showing a shim placing step according to Embodiment 1.

FIG. 10 shows a cover attaching step according to Embodiment 1.

FIG. 17 is a plan view showing the configuration of the conventional radiation tomography apparatus.

DESCRIPTION OF REFERENCES

Figure 1:
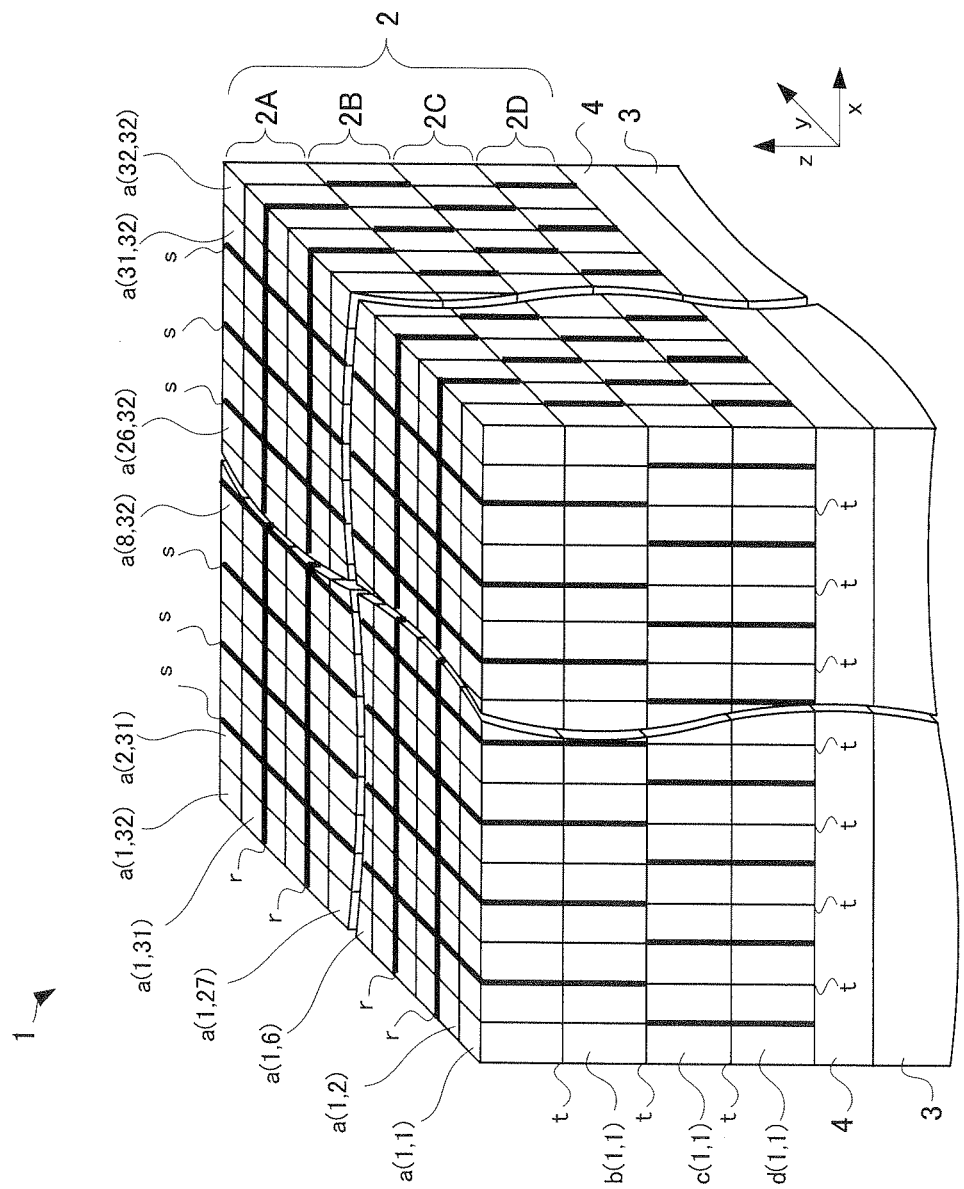
FIG. 1 is a perspective view of a radiation detector according to Embodiment 1.

1a . . . first radiation detector
1b . . . second radiation detector
2a . . . first scintillator
2b . . . second scintillator
3a . . . first light detector
3b . . . second light detector
12 . . . detector ring
14 . . . detector array
15 . . . support tool
18 . . . shim
19 . . . detector unit
25 . . . cover
27 . . . marking (second mark)
30 . . . alignment jig
30b . . . marking (first mark)

DESCRIPTION OF THE PREFERRED EMBODIMENTS

Embodiments of a method of manufacturing radiation tomography apparatus according to this invention will be described hereinafter with reference to the drawings.

Embodiment 1

Firstly, prior to explanation of a method of manufacturing radiation tomography apparatus according to Embodiment 1, description will be given of a configuration of a radiation detector 1 according to Embodiment 1. FIG. 1 is a perspective view of the radiation detector according to Embodiment 1. As shown in FIG. 1, the radiation detector 1 according to Embodiment 1 includes a scintillator 2 that is formed of scintillation counter crystal layers each laminated in order of a scintillation counter crystal layer 2D, a scintillation counter crystal layer 2C, a scintillation counter crystal layer 2B, and a scintillation counter crystal layer 2A, in turn, in a z-direction, a photomultiplier tube (hereinafter referred to as a light detector) 3 having a function of position discrimination that is provided on an undersurface of the scintillator 2 for detecting fluorescence emitted from the scintillator 2, and a light guide 4 interposed between the scintillator 2 and the light detector 3. Consequently, each of the scintillation counter crystal layers is laminated in a direction toward the light detector 3. Here, the scintillation counter crystal layer 2A corresponds to an incident surface of radiation in the scintillator 2. Each of the scintillation counter crystal layers 2A, 2B, 2C, and 2D is optically coupled, and includes a transparent material t between each of the layers. A thermosetting resin composed of a silicone resin may be used for the transparent material t. The scintillation counter crystal layer 2A corresponds to a receiver of the gamma rays emitted from a radioactive source. The scintillation counter crystals in a block shape are arranged in a two-dimensional array with thirty-two numbers of the scintillation counter crystals in an x-direction and thirty-two numbers of the scintillation counter crystals in a y-direction relative to a scintillation counter crystal a (1, 1). That is, the scintillation counter crystals from a (1, 1) to a (1, 32) are arranged in the y-direction to form a scintillator crystal array. Thirty-two numbers of the scintillator crystal arrays are arranged in the x-direction to form a scintillation counter crystal layer 2A. Here, as for the scintillation counter crystal layers 2B, 2C, and 2D, thirty-two numbers of the scintillator counter crystals are also arranged in the x-direction and the y-direction in a matrix in a two-dimensional array relative to a scintillation counter crystal b (1, 1), c (1, 1), and d (1, 1), respectively. In each of the scintillation counter crystal layers 2A, 2B, 2C, and 2D, the transparent material t is also provided between the scintillation counter crystals adjacent to each other. Consequently, each of the scintillation counter crystals is to be enclosed with the transparent material t. The transparent material t has a thickness around 25 µm. The x-direction and the y-direction correspond to the first direction and the second direction, respectively, in this invention. A gamma ray corresponds to radiation in this invention.

First reflectors r that extend in the x-direction and second reflectors s that extend in the y-direction are provided in the scintillation counter crystal layers 2A, 2B, 2C, and 2D provided in the scintillator 2. Both reflectors r and s are inserted in a gap between the arranged scintillation counter crystals.

The scintillator 2 has scintillation counter crystals suitable for detection of gamma rays in a three-dimensional array. That is, the scintillation counter crystal is composed of Ce-doped $Lu_{2(1-X)}Y_2XSiO_5$ (hereinafter referred to as LYSO.) Each of the scintillation counter crystals is, for example, a rectangular solid having a length of 1.45 mm in the x-direction, a width of 1.45 mm in the y-direction, and a height of 4.5 mm regardless of the scintillation counter crystal layer. The scintillator 2 has four side end faces that are covered with a reflective film not shown. The light detector 3 is multi-anode type, and allows position discrimination of incident fluorescence in the x and y.

Figure 2:
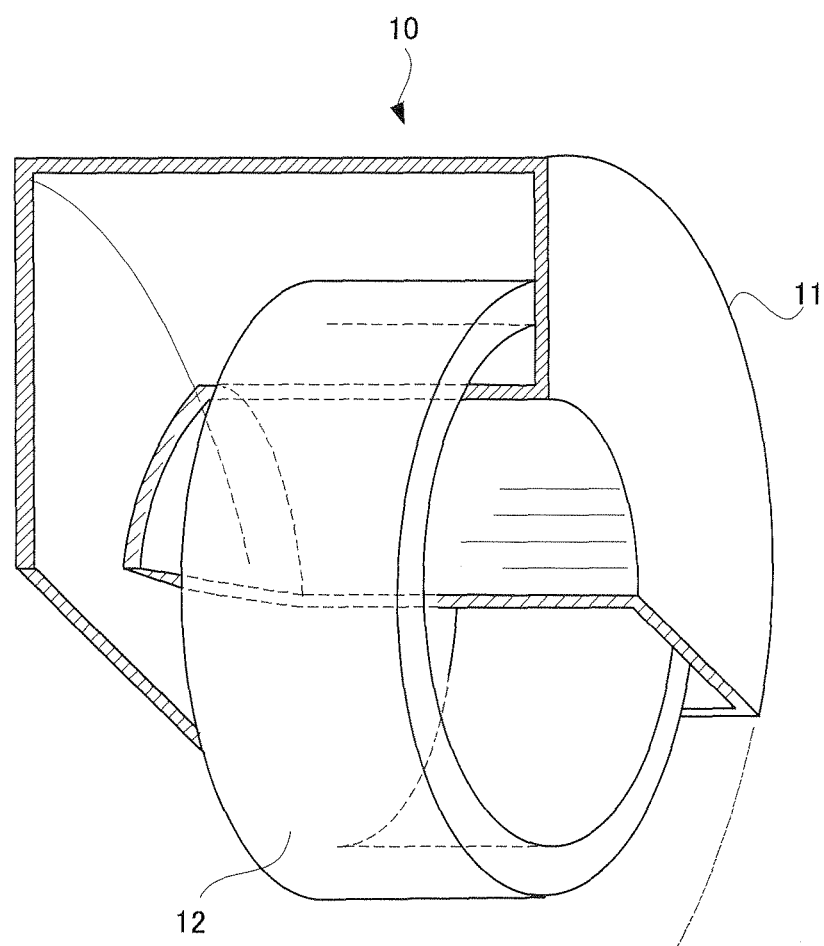
FIG. 2 is a sectional cut-away view showing a configuration of radiation tomography apparatus according to Embodiment 1.

Next, description will be given of a configuration of radiation tomography apparatus 10 according to Embodiment 1. FIG. 2 is a sectional cut-away view showing a configuration of the radiation tomography apparatus according to Embodiment 1. As shown in FIG. 2, the radiation tomography apparatus 10 according to Embodiment 1 has a gantry 11 having an opening for introducing a subject, and a detector ring 12 in a circular ring shape that is provided inside the gantry 11 so as to contain the opening of the gantry 11. Gamma rays emitted from the subject enter into the detector ring 12. The detector ring 12 in the radiation tomography apparatus 10 determines intensity, an incidence period of time, and an incidence position of incident gamma rays.

Figure 3:
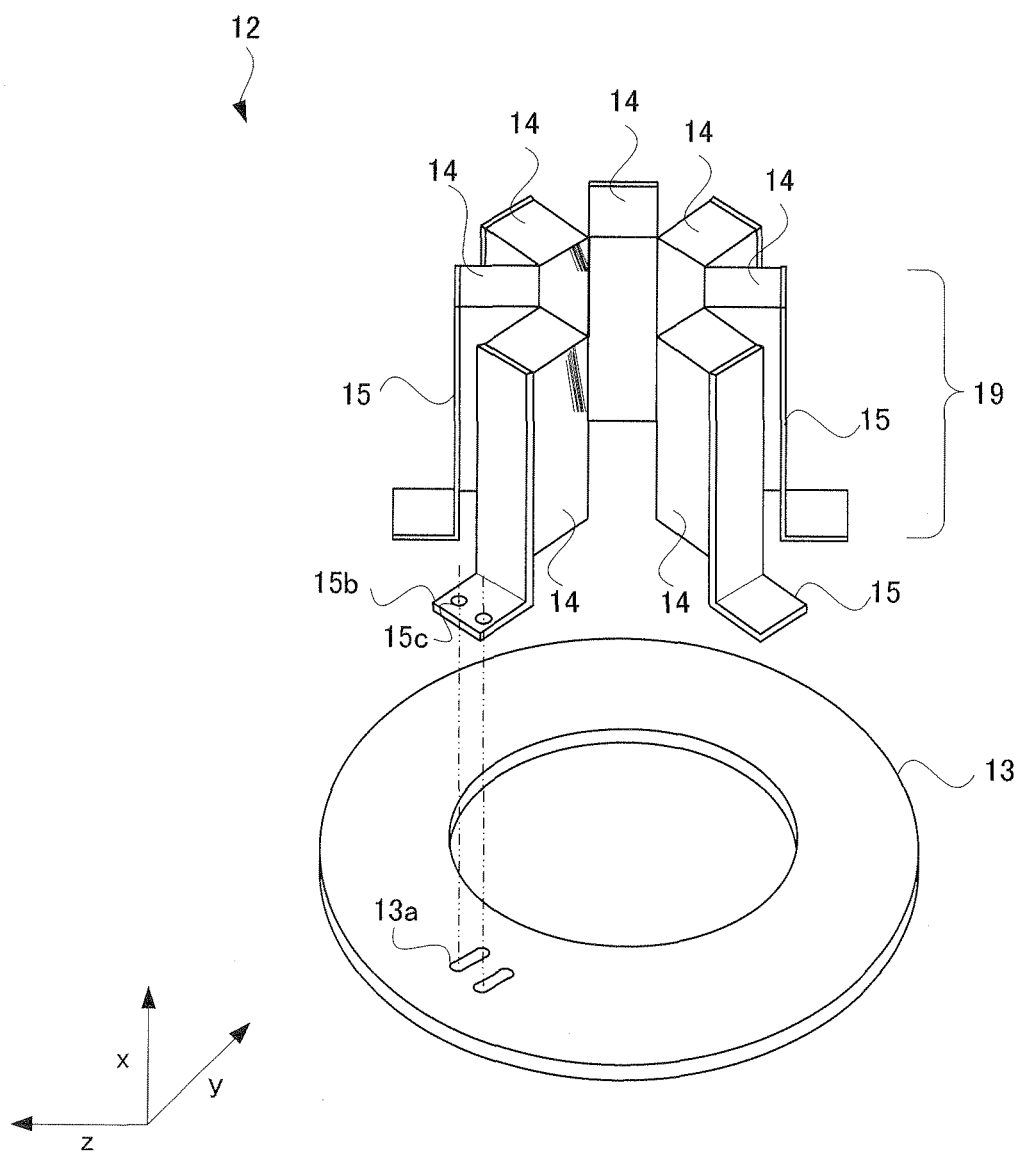
FIG. 3 is an exploded perspective view showing a configuration of a detector ring according to Embodiment 1.
Figure 4:
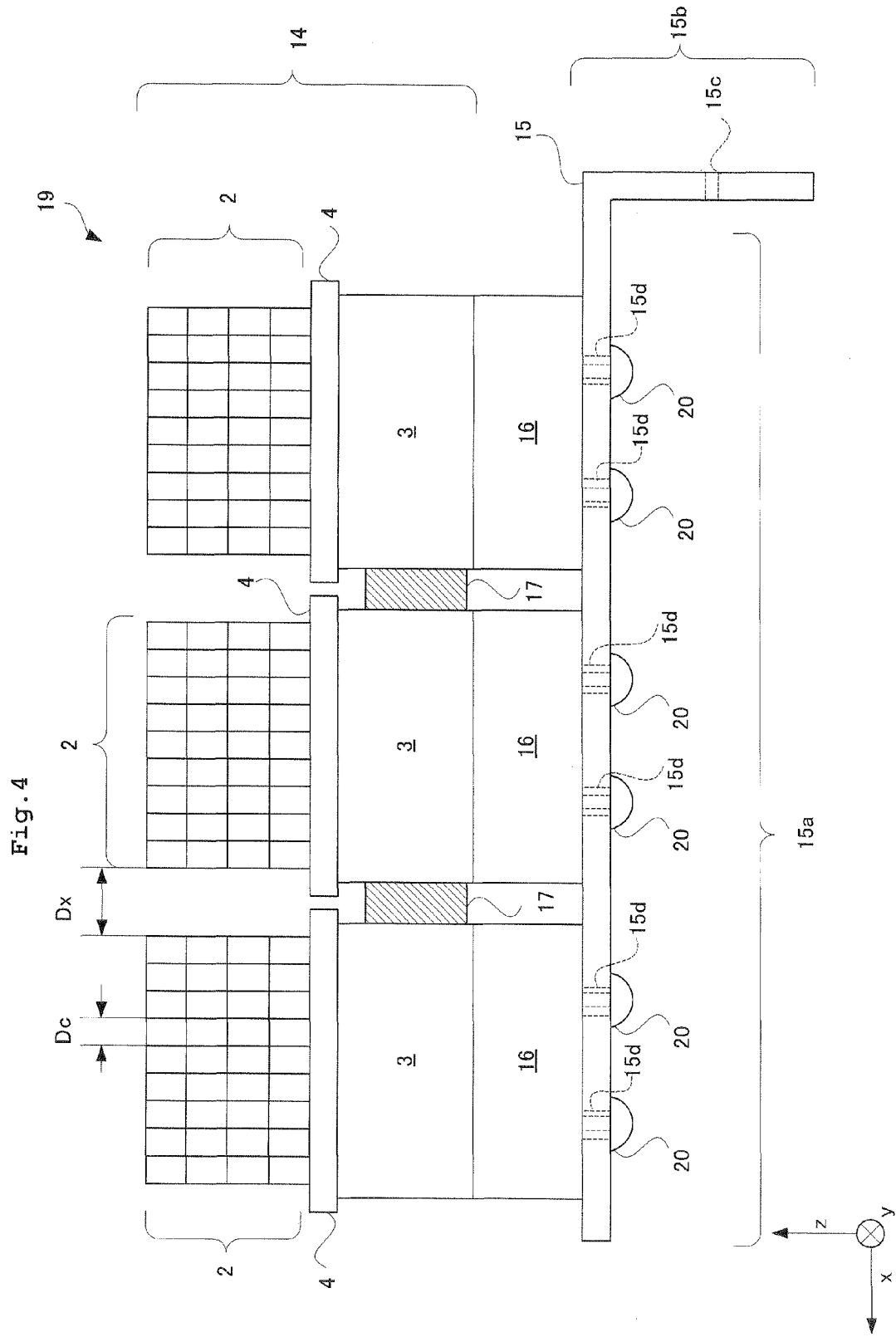
FIG. 4 is a plan view showing a configuration of a detector unit according to Embodiment 1.

Description will be given of a configuration of the detector ring 12. FIG. 3 is an exploded perspective view showing a configuration of the detector ring according to Embodiment 1. As shown in FIG. 3, the detector ring 12 has two or more detector units 19 arranged annularly on a bottom plate 13 in a ring shape. As shown in FIG. 4, in the detector unit 19, a detector array 14 having three radiation detectors 1 arranged in series in the x-direction and an L-shaped support tool 15 are coupled in the z-direction.

Seen the detector ring 12 in the x-direction, the scintillators 2 provided in the detector unit 19 are arranged so as to face toward inside of the bottom plate 13. Accordingly, the scintillators 2 cover the inside of the detector ring 12. Here in FIG. 3, only seven detector units 19 are shown since the detector unit 19 on the most front side is omitted for expediency of explanation. Actually, eight detector units 19 are annularly arranged. In addition, the detector unit 19 is fastened to the bottom plate 13 via a sub-plate 15b, mentioned later, with a bolt and a nut. The bottom plate 13 has a long hole 13a through which the bolt penetrates with respect to each detector unit 19.

Description will be given of a configuration of the detector unit 19. FIG. 4 is a plan view showing a configuration of the detector unit according to Embodiment 1. As shown in FIG. 4, the detector unit 19 has three radiation detectors arranged in series in the x-direction. Specifically, the detector unit 19 has an L-shaped support tool 15, a bleeder unit 16 that is coupled to the support tool 15 in the z-direction and provided with a bleeder circuit for supplying voltages to the radiation detector 1, and the radiation detector 1 that is connected to the bleeder unit 16 so as to extend in the z-direction. More specifically, the light detector 3 in the radiation detector 1 is connected to the bleeder unit 16. Such configuration allows the bleeder unit 16 to supply voltages directly to the light detector 3. Moreover, the detector unit 19 has three light detectors 3 that are joined via a plate spacer 17 in the x-direction. The spacer 17 determines a position of the radiation detector 1 in the detector unit 19 according to Embodiment 1, which is to be described hereinafter in detail. The scintillator 2 in FIG. 4 has nine scintillation counter crystals arranged in the x-direction. This is due to simplification of the drawing for suitable explanation. Actually, the scintillator 2 has thirty-two scintillation counter crystals arranged in the x-direction. Three scintillators 2 of the detector unit 19 are integrally covered with a cover 25, not shown, made from aluminum, etc.

The support tool 15 is L-shaped. Three radiation detectors 1 are connected to a main plate 15a of the support tool 15 that extends in the x-direction. The sub-plate 15b that is smaller than the main plate 15a extends at right angle from one end of the main plate 15a in the z-direction. The sub-plate 15b is a member for fixing the support tool 15 on the bottom plate (see FIG. 3), and has a screw hole 15c formed therein for connecting the bottom plate 13. On the other hand, the main plate 15a has a drilled hole 15d formed therein for connection to the bleeder unit 16. The support tool 15 reaches the bleeder unit 16 by penetration of a screw 20 through the drilled hole 15d. The bleeder unit 16 is provided with a screw hole that conforms to the screw 20. The bleeder unit 16 and main plate 15a are integrated by fastening each of the screws 20. Here, the drilled hole 15d provided in the main plate 15a has a larger diameter than a shank of the screw 20 so as to realize alignment of the bleeder unit 16. The drilled hole 15d has a smaller diameter than a head of the screw 20.

Next, description will be given of clearance Dx between adjacent scintillators 2 in the detector unit 19 with reference to FIG. 4. The scintillator 2 has two or more scintillation counter crystals arranged in a three-dimensional array. Assuming that an arrangement pitch of the scintillation counter crystals in the scintillator 2 be Dc, the clearance Dx of the adjacent scintillators 2 is of integral multiples of the arrangement pitch Dc. For instance, assuming that the arrangement pitch of the scintillators be of 1.5 mm, the clearance Dx is of 3 mm. That is, in the configuration of Embodiment 1, the clearance Dx is twice the clearance Dc. The gap between the scintillators includes a second reflector s or a transparent material t. Thus, a length of the scintillation counter crystal does not necessarily correspond to the arrangement pitch of the scintillation counter crystal. Here, twice corresponds to integral multiples in this invention.

Figure 5:
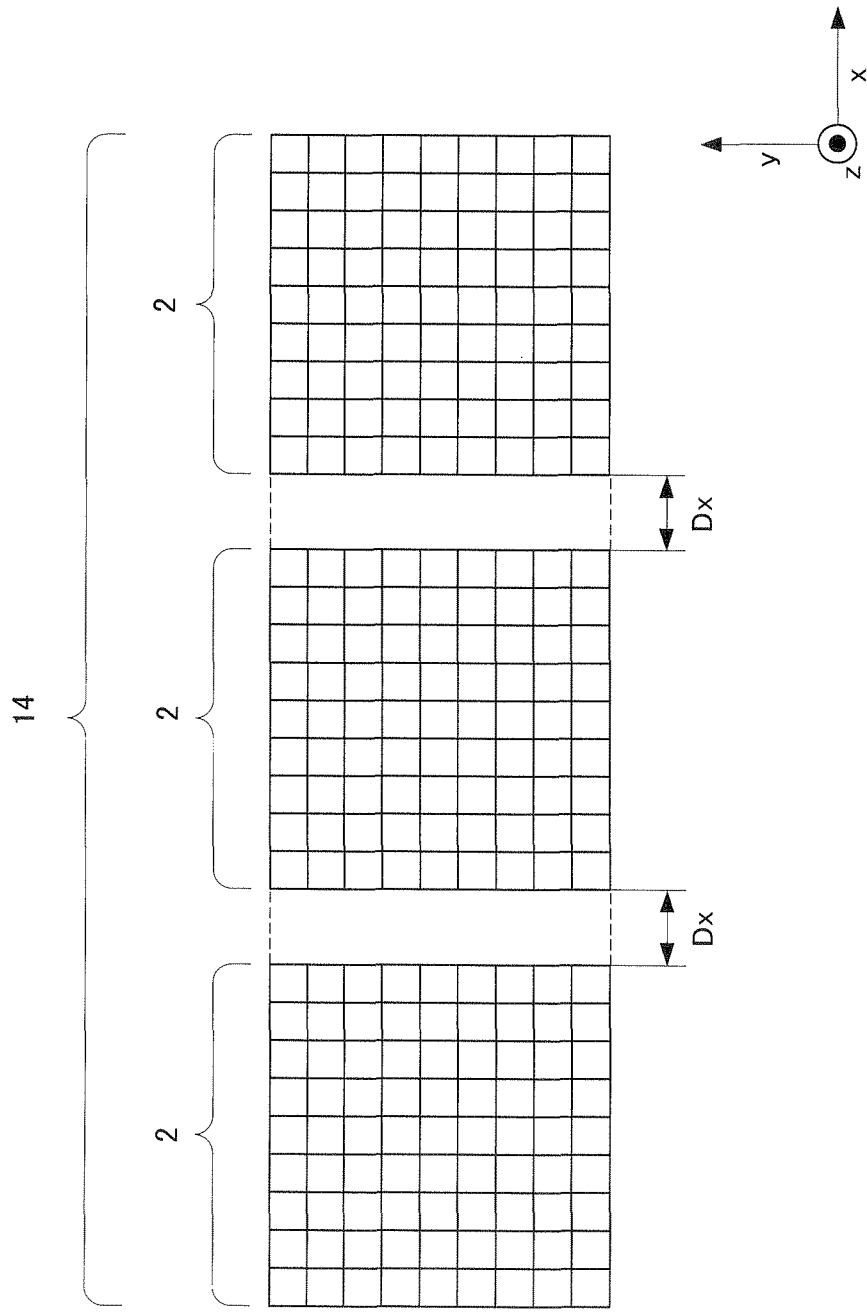
FIG. 5 is a plan view of a detector array according to Embodiment 1 seen from a z-direction thereof.

FIG. 5 is a plan view of the detector array according to Embodiment 1 seen from a z-direction thereof. As shown in FIG. 5, each of the scintillators 2 provided in the detector array 14 has a same position in the y-direction. Taking into consideration that the scintillation counter crystals in each of the scintillators 2 have the same arrangement pitch, arrangement of the scintillation counter crystals does not deviate, and all the scintillation counter crystals provided in the detector array 14 are arranged in a position of the integral multiples of the arrangement pitch Dc. That is, all the scintillation counter crystals have a unified position in x- and y-direction throughout the detector array 14 so as to correspond to the integral multiples of the arrangement pitch Dc. The scintillator 2 in FIG. 5 has nine scintillation counter crystals arranged in the y-direction. This is due to simplification of the drawing for suitable explanation. Actually, the scintillator 2 has thirty-two scintillation counter crystals arranged in the y-direction.

Figure 8:
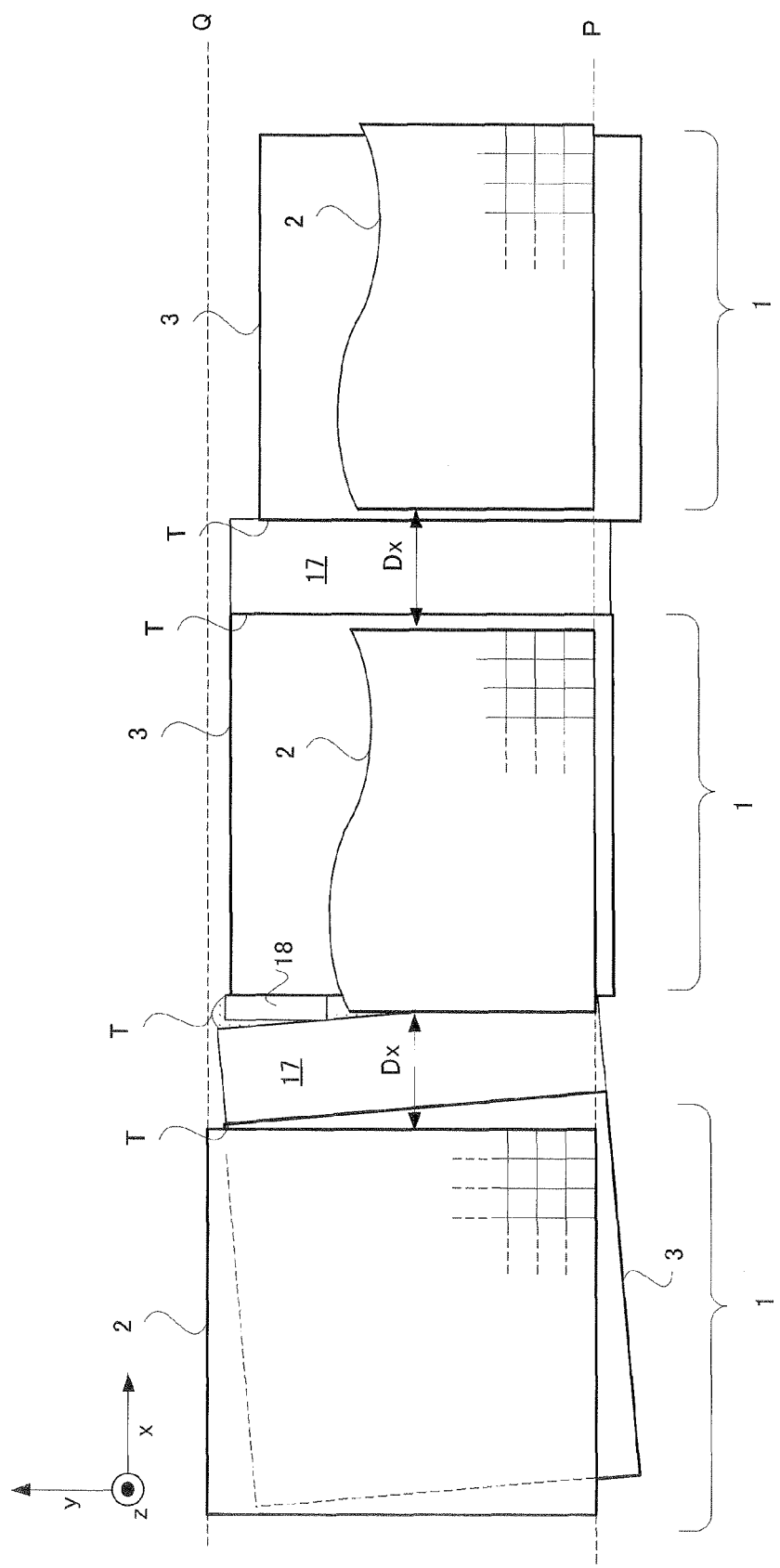
FIG. 8 is a plan view showing the detector array according to Embodiment 1.

Moreover, as shown in FIG. 8, the detector array 14 may include not only the spacer 17 but also a shim 18 at a connection portion of the scintillators 2 adjacent to each other that is capable of adjusting an angle of the light detector 3. The spacer 17 may be composed of metal or Bakelite. In addition, the shim 18 may be composed of a Teflon (registered trademark) tape.

Hereinafter, a bottom face of the radiation detector 1 is covered with a protection socket prior to connection of the radiation detector 1 in the x-direction that is explained with the method of manufacturing the radiation tomography apparatus of such a configuration. Specifically, each of the pins provided on the bottom face of the light detector 3 in the radiation detector 1 is covered with the protection socket, whereby the bottom face of the radiation detector 1 is protected with the protection socket.

<Preliminary Arranging Step>

According to the configuration of Embodiment 1, the radiation detector 1 has the light detectors 3 joined to each other via the spacer 17. Seen the radiation detector 1 in the z-direction, a relative position of the light detector 3 to the scintillator 2 deviates depending on the radiation detector 1. In the preliminary arranging step, the spacer 17 is selected such that the deviation is accommodated and the clearance Dx between both scintillators 2 of the radiation detector adjacent to each other is set Dx. The spacers 17 having various thicknesses are formed in advance, and one of them is to be used for connecting the radiation detectors.

FIG. 6 is a plan view showing a preliminary arranging step according to Embodiment 1. For simpler explanation on this step, it is assumed that the first radiation detector 1a and the second radiation detector 1b be connected in the x-direction, the first radiation detector 1a have the first scintillator 2a and the first light detector 3a, and likewise the second radiation detector 1b have the second scintillator 2b and the second light detector 3b. It is further assumed that a side surface among the side surfaces of the first scintillator 2a that faces to the second radiation detector 1b be a scintillator side surface 22a, and likewise a side surface among the side surfaces of the first light detector 3a that faces to the second radiation detector 1b be a light detector side surface 23a. It is further assumed that a side surface among the side surfaces of the second scintillator 2b that faces to the first radiation detector 1a be a scintillator side surface 22b, and likewise a side surface among the side surfaces of the second light detector 3b that faces to the first radiation detector 1a be a light detector side surface 23b.

Firstly, in the preliminary arranging step as shown in FIG. 6(a), both scintillators 2 are actually spaced away by the clearance Dx to read the clearance T between both lights detectors 3 at this time. As shown in FIG. 6(a), the relative position of the light detector 3 to the scintillator 2 deviates depending on the radiation detector 1. In this step, a position and a direction of both radiation detectors 1a and 1b are adjusted such that the clearance Dx between the first scintillator 2a and the second scintillator 2b is twice the arrangement pitch of the scintillation counter crystal in the x-direction and both scintillator side surfaces 22a and 22b are parallel. Here, it is assumed that a clearance at this time between both light detector side surfaces 23a and 23b be T. Then, a spacer 17 is selected that has a thickness nearest to the clearance T. In addition, the spacer 17 has a width in the y-direction approximately equal to that of both light detector side faces 23a and 23b. As shown in FIG. 6(b), when the light detector 3 is tortuously coupled to the scintillator 2 or has a trapezoidal shape, and both light detector side surfaces 23a and 23b are not parallel, a nearest portion between both light detector side surfaces 23a and 23b be the clearance T. Specifically, the clearance T is a clearance between a side 33a of the light detector 3b that projects toward the light detector 3b and the light detector side surface 23b of the light detector 3b.

<First Spacer Joining Step>

The clearance T is determined and the spacer 17 is selected. Thereafter, both radiation detectors 1a and 1b are temporarily spaced away such that the spacer 17 is joined as to cover the light detector side surface 23a in the first radiation detector 1a that faces in the x-direction. Here, the x-direction corresponds to the first direction in this invention.

<Shim Placing Step>

The method of manufacturing the radiation tomography apparatus according to Embodiment 1 may include a shim placing step as required. As shown in FIG. 6(b), this is a step of arranging the shim 18 that adjusts the opposite angle of both scintillators 2a and 2b in a position between the spacer 17 and the second radiation detector 1b where both light detector side surfaces 23a and 23b are not parallel. FIG. 7 is a plan view showing a shim placing step according to Embodiment 1. In this step, as shown in FIG. 7(a), the second radiation detector 1b firstly approaches the spacer 17 joined to the first radiation detector 1a in the x-direction, thereby contacting the light detector side surface 23b of the light detector 3b to the spacer 17. Here, the clearance Dx between both scintillators 2a and 2b is of integral multiples (twice in Embodiment 1) of the arrangement pitch of the scintillator. Thereafter, the second radiation detector 1b is inclined with respect to the first radiation detector 1a to correct an opposite angle of both scintillators 2a and 2b, whereby the second radiation detector 1b is arranged such that both scintillator side surfaces 22a and 22b are parallel. On the other hand, the spacer 17 and the light detector 3b are not parallel, and a V-shaped gap is to be formed therebetween. Then, the shim 18 is prepared that has a suitable thickness for interpolating the gap, and is inserted into the V-shaped gap.

<Second Spacer Joining Step>

An adhesive is applied to the light detector side surface 23b. Then, the light detector side surface 23a is approached to the spacer 17 joined to the light detector side surface 23a in the x-direction. Here, not an adhesive that hardens in an instant but an adhesive that requires a given period of time for hardening is desirable. Thereafter, the second radiation detector 1b is moved in the y-direction such that both scintillators 2a and 2b have a same position in the y-direction to each other. This operation is done under the microscope such that both scintillators 2a and 2b have a same position correctly in the y-direction. Then, the adhesive is hardened to complete this step. As noted above, one side surface of the light detector 3a provided in the first radiation detector 1a is joined to one side surface of the second light detector 3b provided in the second radiation detector 1b via the spacer 17, thereby forming a detector array extending in the x-direction. Here, in the detector array 14 according to Embodiment 1, a third radiation detector is coupled via the spacer 17 to a side surface 23c that faces to the light detector side surface 23b in the light detector 3b provided in the second radiation detector 1b, which achieves three radiation detectors arranged in the x-direction. The situation of coupling the second radiation detector 1b to the third radiation detector is similar to that in each of the foregoing steps, and thus the explanation thereon is to be omitted. As above, the detector array 14 according to Embodiment 1 is formed.

FIG. 8 is a plan view showing the detector array according to Embodiment 1. As shown in FIG. 8, the detector array 14 according to Embodiment 1 is formed with reference to the scintillator 2. Specifically, the clearance Dx between each scintillator 2 in the x-direction is twice the arrangement pitch of the scintillation counter crystals in the x-direction, and each scintillator 2 has a same position in the y-direction. Consequently, each scintillator 2 has a same position P in one side end thereof in the y-direction that faces the y-direction. Moreover, each scintillator 2 has a same position Q in other side end thereof in the y-direction that faces the y-direction. The scintillation counter crystals have a unified position in x- and y-directions throughout the detector array 14, and are arranged regularly over two or more scintillators 2 that form the detector array 14. That is, the detector array 14 has a configuration in which one hundred scintillation counter crystals in the x-direction and thirty-two scintillation counter crystals in the y-direction are arranged two-dimensionally, and thereafter, the scintillation counter crystals located in the thirty-third, the thirty-fourth, the sixty-seventh, and the sixty-eighth in the x-direction are removed that extend in the y-direction.

Moreover, in the configuration in FIG. 8, one side surface of the light detector 3 is joined to the spacer 17 via an adhesive T. A release agent may be applied in advance to the shim 18 prior to the second spacer joining step, thereby the shim 18 may be pulled out in the y-direction to be removed from the detector array 14.

<Detector Ring Forming Step>

The method of manufacturing the radiation tomography apparatus according to Embodiment 1 includes a detector ring forming step that arranges the detector array annularly to form the detector ring. Specifically, the detector ring forming step includes a detector unit manufacturing step of manufacturing a detector unit 19 by fixing the radiation detector that constitutes the detector array 14 to a support tool 15 that extends in the x-direction, a cover attaching step of attaching a cover 25 for covering an upper surface of the scintillators 2 of the detector unit 19, a detector unit placing step of placing the detector units 19 from an upper direction such that the scintillators are directed toward inside of the ring-shaped bottom plate 13, thereby arranging the detector units 19 annularly in the circular ring having an inner hole that extends in the x-direction, an alignment jig placing step of placing a columnar alignment jig 30 from the inner hole, and a detector unit fixing step of fixing the detector unit 19 on the bottom plate 13 by determining a position of the detector unit 19 with respect to the alignment jig 30. Description of each step mentioned above will be made in order for explanation on the detector ring forming step.

<Detector Unit Manufacturing Step>

Figure 9:
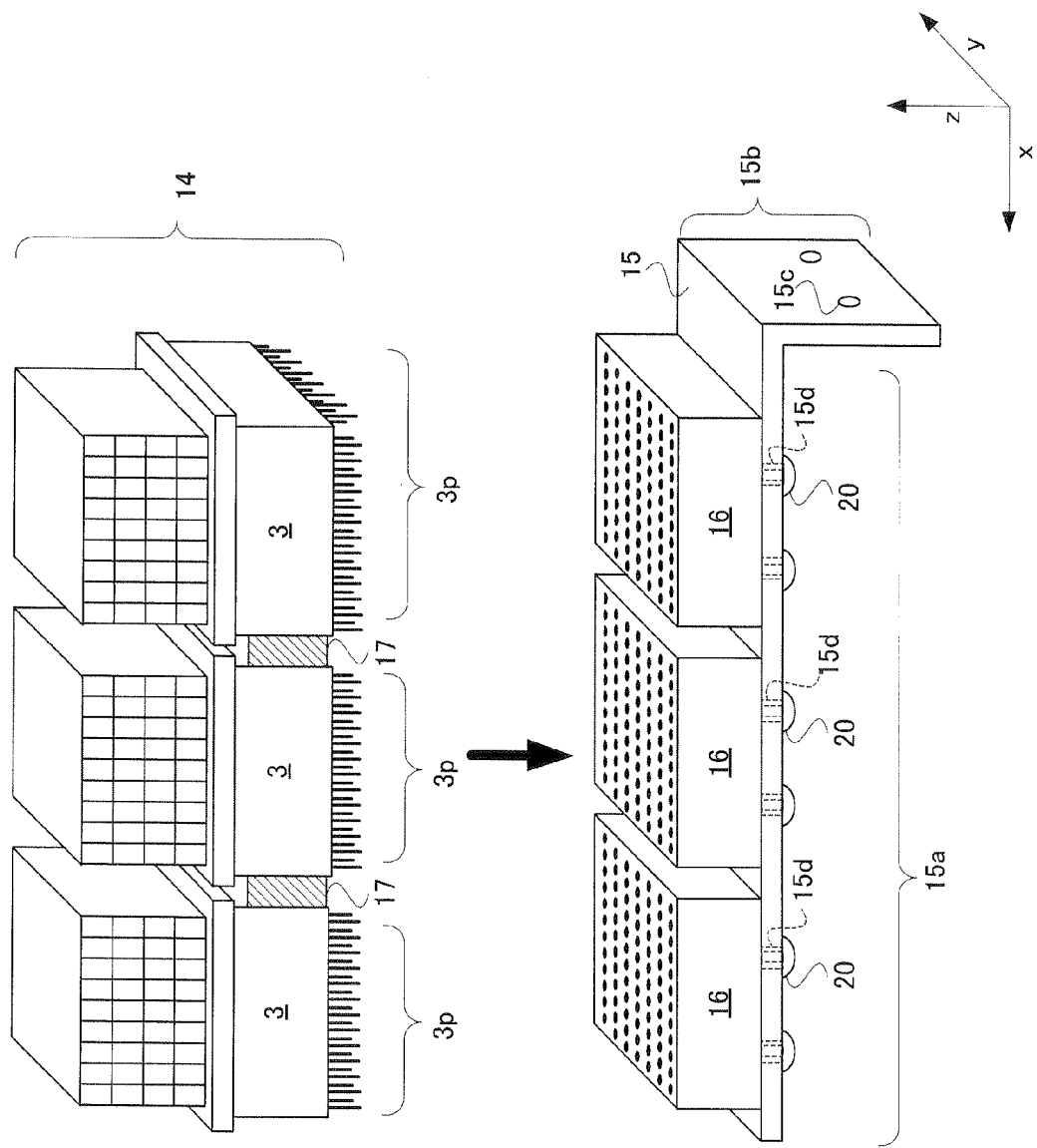
FIG. 9 is a perspective view showing a method of manufacturing the detector unit according to Embodiment 1.

FIG. 9 is a perspective view showing a method of manufacturing the detector unit according to Embodiment 1. In this step, the detector array 14 having integrated three radiation detectors 1 is fixed on the main plate 15a of the L-shaped support tool 15, thereby forming the detector unit 19. Specifically, the protection socket that covers the bottom face of the radiation detector is removed from the detector array 14. Thereafter, as shown in FIG. 9, each of an exposed pin group 3p is inserted into the socket provided in the top of the three bleeder units 16 arranged in advance on the main plate 15a. Here, the bleeder unit 16 and the main plate 15a are connected via the screw 20, but the screw 20 is loose. The drilled holes 15d in the main plate 15a through which the screw 20 is penetrated has a larger diameter than the shank of the screw 20. Consequently, the relative position of the bleeder unit 16 with respect to the main plate 15a may be adjusted. In other words, the pin group 3p in the radiation detector may be inserted into the socket with the three bleeder units 16 being adjusted in position. As for operation, seen the detector unit 19 in the z-direction, alignment is performed such that a center line of the main plate 15a conforms to a center line of the scintillator arrays along the x-direction. Thereafter, the screw 20 is fastened to integrate the detector array 14 and the support tool 15. As noted above, the detector unit 19 is completed.

<Cover Attaching Step>

The detector unit 19 has three scintillators 2. In the cover attaching step, the cover 25 is attached that covers entirely the three scintillators 2. FIG. 10 shows a cover attaching step according to Embodiment 1. As shown in FIG. 10(a), the cover 25 has a rectangular shape with an opening that opens forward in the z-direction. The opening of the cover 25 is set so as to have a length in the x-direction longer than the scintillator array. Specifically, assuming that the scintillator has a length in the x-direction and a width in the y-direction of 48 mm and clearance Dx therebetween of 3 mm, the opening of the cover 25 is set to have a length Da in the x-direction longer than a total amount 150 mm, i.e., a total of 144 mm, which corresponds to the length of three scintillators 2, and 6 mm, which is a total of clearance of three scintillators 2. Moreover, the opening of the cover 25 is set to have a larger width Db than 48 mm as a width of the scintillator 2 in the y-direction. Furthermore, the opening of the cover 25 is set to have a depth Dd in the z-direction that is deep enough for the cover 25 to cover the scintillator 2 completely. The cover 25 is made from aluminum etc., for covering the scintillator 2 for protection.

As shown in FIG. 10(a), in the cover attaching step, plate cover spacers 26a, 26b, and 26c are placed so as to cover three side surfaces of the scintillator 2p that is arranged in a farthest position from the sub-board 15b provided in the support tool 15. Thereafter, the cover 25 approaches in the z-direction so as to cover the three scintillators 2. Here, the opening of the cover 25 is set to have the width Db in the y-direction larger than the width of the scintillator 2 in the y-direction. Consequently, a gap may occur in the y-direction between the scintillator 2 and the opening of the cover 25. The plate cover spacers 26a and 26b that extend in the x- and z-directions may fill in the gap. The relative position of the scintillator 2 and the cover 25 in the y-direction may be adjusted by changing a thickness of the cover spacers 26a and 26b in the y-direction. Specifically, the relative position of the scintillator 2 and the cover 25 in the y-direction is adjusted such that a center of the cover 25 in the y-direction conforms to a center of the scintillator array in the y-direction. Likewise, the plate cover spacer 26c that extends in the y- and z-directions is provided for adjusting the relative position of the scintillator 2 and the cover 25 in the x-direction. Description will be given hereinafter of determination of the cover spacer 26 in thickness in the x-direction.

FIG. 10(b) is a plan view showing a configuration of the cover according to Embodiment 1 in the xy plane. As shown in FIG. 10(b), the cover 25 has a marking 27 in one side surface thereof that extends in the z-direction. The marking 27 indicates a center of the cover 25 in the y-direction. The relative position of the scintillator 2 and the cover 25 in the y-direction is set such that a center thereof in the y-direction conform to each other. Accordingly, the marking 27 indicates not only the center of the cover 25 in the y-direction but also the center of the scintillator 2 in the y-direction. Let one side end of the cover 25 having the marking 27 provided therein be an alignment side end 25a of the cover 25. A direction where the alignment side end 25a are spaced away from the sub-board 15b is selected as a direction for attaching the cover 25. Here, the marking 27 corresponds to the second mark in this invention.

<Detector Unit Placing Step>

Figure 11:
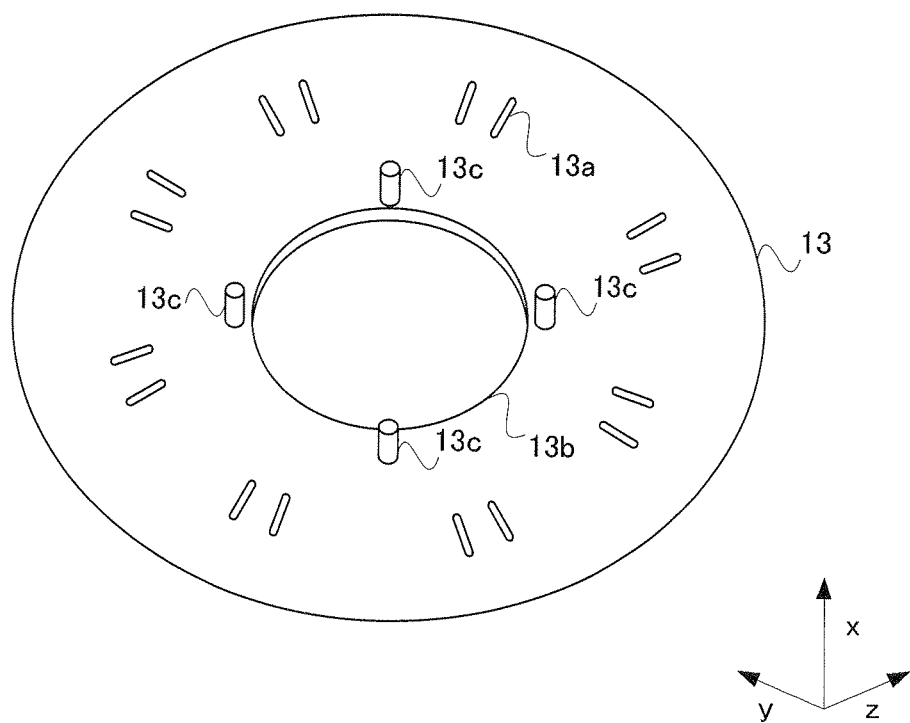
FIG. 11 is a perspective view showing a configuration of a bottom plate according to Embodiment 1.

Description will be given next of the detector unit placing step. Prior to this, the detector unit is placed on the bottom plate 13. Thus, description will be firstly given of a configuration of the bottom plate 13. FIG. 11 is a perspective view showing a configuration of a bottom plate according to Embodiment 1. As shown in FIG. 11, the ring-shaped bottom plate 13 with an inner hole 13b formed inside thereof has long holes 13a arranged annularly. In addition, for instance, four nibs 13c that project in the x-direction are arranged annularly along the inner hole 13b at an inner periphery of the ring-shaped bottom plate 13.

Figure 12:
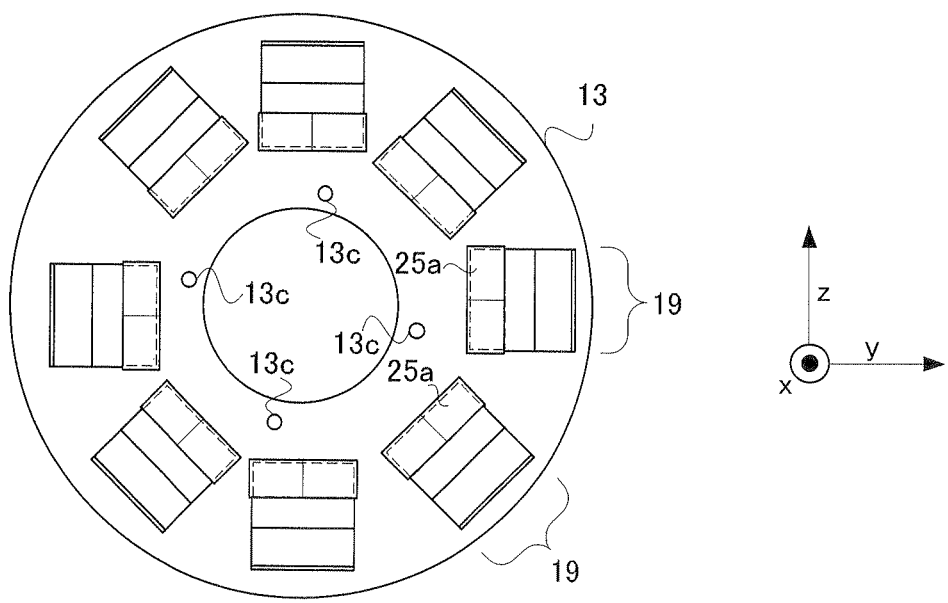
FIG. 12 is a plan view showing a detector unit placing step according to Embodiment 1 seen from an x-direction thereof.

FIG. 12 is a plan view showing a detector unit placing step according to Embodiment 1 seen from an x-direction. As shown in FIG. 12, the detector units 19 are arranged annularly on the bottom plate 13. Here, the sub-board 15b of the detector unit 19 contacts the bottom plate 13. A bolt is screwed into the screw hole 15c provided in the sub-board 15b. Then, the shank of the bolt is penetrated through the long hole 13a in the bottom plate 13. Thereafter, the shank of the bolt is screwed into a nut provided on a rear face of the bottom plate 13, which situation is as shown in FIG. 3. The bolt and the nut are loose in this state. Accordingly, the position of the detector unit 19 with respect to the bottom plate 13 may be somewhat be adjusted.

<Alignment Jig Placing Step>

Figure 13:
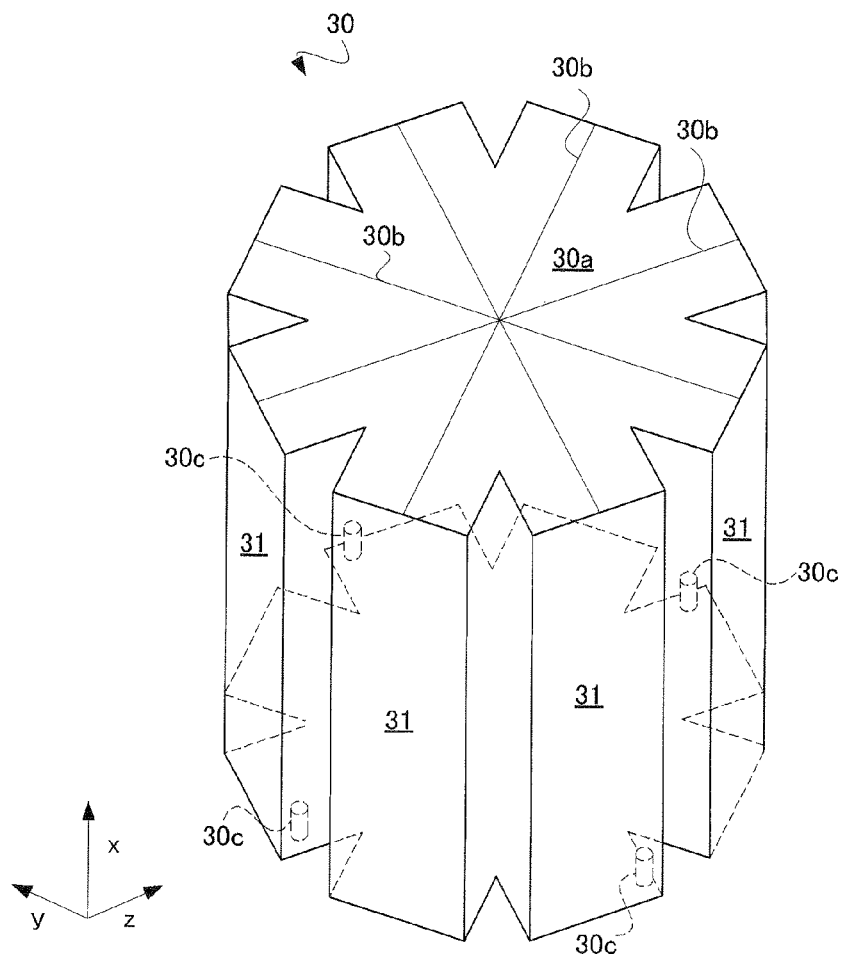
FIG. 13 is a plan view showing a configuration of an alignment jig according to Embodiment 1.

In the alignment jig placing step, a columnar alignment jig 30 that extends in the x-direction is placed inside the circular ring formed by the detector units 19. Firstly, description will be given of a configuration of the alignment jig 30 according to Embodiment 1 prior to explanation on this step. FIG. 13 is a perspective view showing a configuration of an alignment jig according to Embodiment 1. As shown in FIG. 13, the alignment jig 30 has a column shape extending in the x-direction having eight-fold rotational symmetry in the x-direction. Moreover, the alignment jig 30 has on the side surface thereof contact surfaces 31 of the same number as the detector units 19 to be placed in the bottom plate 13. Specifically, eight detector units 19 are placed on the bottom plate 13, and accordingly, the alignment jig 30 has eight contact surfaces 31.

The alignment jig 30 has eight markings 30b on an upper surface 30a thereof. The markings 30b are radially provided from a center of the alignment jig 30, and each of them indicates a center of each contact surface 31. Moreover, seen the alignment jig 30 in the x-direction, the eight markings 30b have a radial pattern of eight-fold rotational symmetry. In addition, the contact surfaces 31 of the alignment jig have eight-fold rotational symmetry. Seen the alignment jig in the x-direction, a center of the rotational symmetry is identical to a center of the radial pattern of the marking 30b. The marking 30b provided in the alignment jig 30 corresponds to the first mark in this invention.

Figure 14:
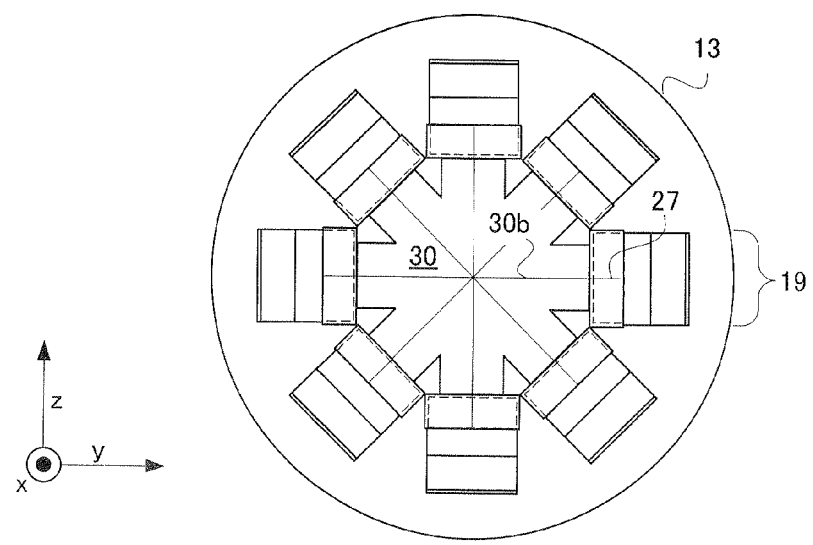
FIG. 14 is a plan view showing an alignment jig placing step and a detector unit fixing step according to Embodiment 1.

The alignment jig 30 has, for example, four slits 30c in the bottom face thereof. Each of the four nibs 13c provided on the bottom plate 13 may be fitted into each of the slits 30c. FIG. 14 is a plan view showing an alignment jig placing step and a detector unit fixing step according to Embodiment 1. In the alignment jig placing step, the alignment jig 30 is inserted inside the circular ring formed by the detector units 19 in the x-direction, and then placed on the bottom plate 13. Here, each of the nibs 13c on the bottom plate 13 is inserted into the slit 30 provided in the bottom surface 13 of the alignment jig 30 for placing the alignment jig 30 in a given position in the bottom plate 13. Specifically, the position of the nib 13c and the slit 30c is determined such that the center of the ring-shaped bottom plate 13 and a rotation axis of the alignment jig 30 overlap one another.

<Detector Unit Fixing Step>

Next, a position of the detector unit 19 in the bottom plate 13 is determined, and the detector unit 19 is fixed on the bottom plate 13. Specifically, the radiation detector unit 19 slides in a direction perpendicular to the marking 30b while the contact surface 31 of the alignment jig 30 contacts the cover 25 of the radiation detector unit 19, whereby the position of the radiation detector unit 19 is determined. More specifically, the position of the radiation detector unit 19 is adjusted such that the position of the marking 30b in the alignment jig 30 conforms to that of the marking 27 in the cover 25. Upon completion of adjustment of the detector unit 19, the bolt and nut are fastened that are provided in the sub-board 15b of the detector unit 19 to fix the detector unit 19 on the bottom plate 13. Accordingly, the position of the detector unit 19 in the bottom plate 13 is to be determined. When such determination in position is performed to every detector unit 19, the detector units 19 may be arranged on the bottom plate so as to correctly have eight-fold rotational symmetry, as shown in FIG. 14.

Description will be given of determination in thickness in the x-direction of the cover spacer 26c shown in FIG. 10. When the cover spacer 26c has a suitable thickness, arrangement may be realized of the upper end of the cover 25 and the upper end of the alignment jig 30 in a same plane. Such configuration allows easy alignment of the marking 30b in the alignment jig 30 and the marking 27 in the cover 25.

<Subsequent Steps>

Figure 15:
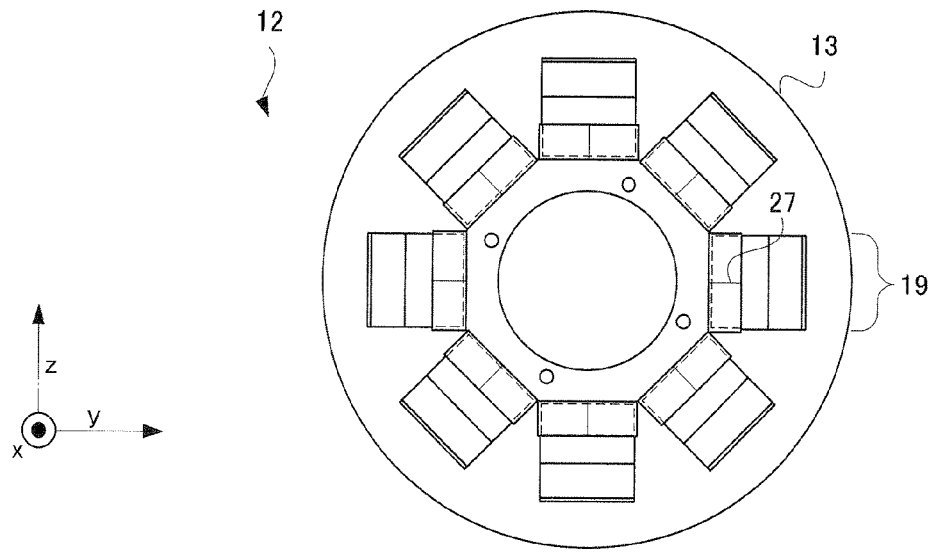
FIG. 15 is a plan view showing a subsequent step according to Embodiment 1.
Figure 16:
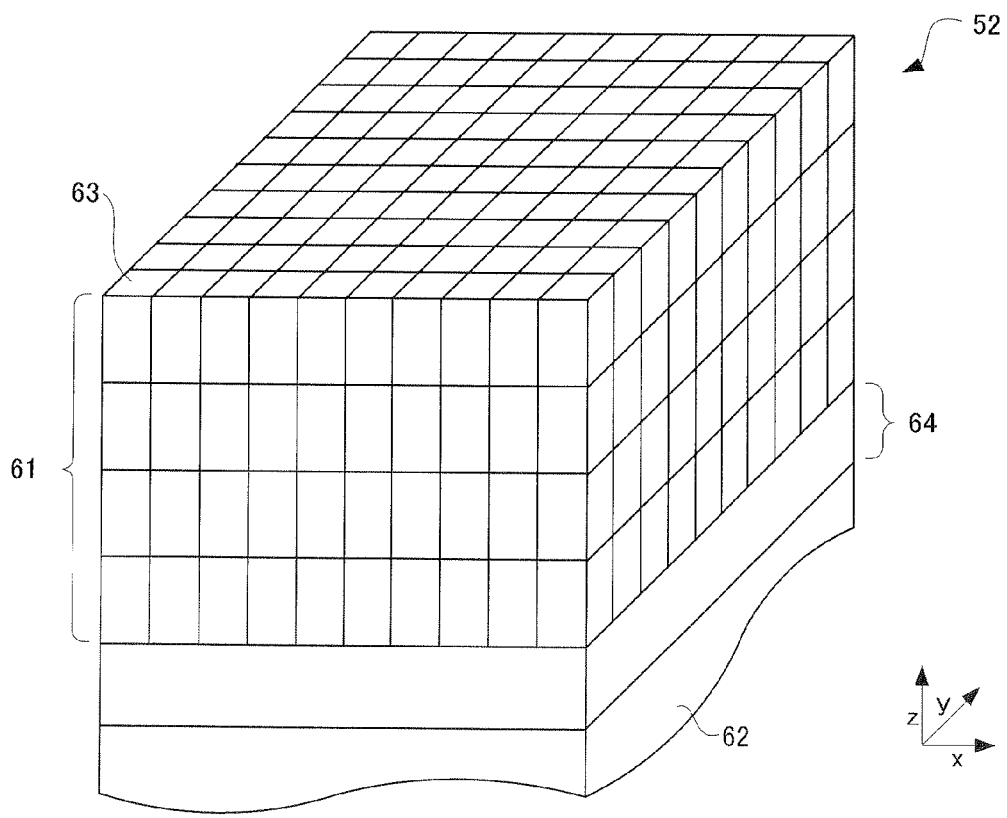
FIG. 16 is a perspective view showing a configuration of conventional radiation tomography apparatus.

Next, the alignment jig 30 is pulled upward in the x-direction and removed from inside of the circular ring. Accordingly, the detector ring 12 as shown in FIG. 15 is manufactured in this way. Finally, the detector ring 12 is mounted in the gantry 11, and thus the radiation tomography apparatus according to Embodiment 1 is accomplished.

As mentioned above, the configuration according to Embodiment 1 may provide the radiation tomography apparatus 10 having higher spatial resolution. The scintillators 2 provided in the radiation tomography apparatus 10 according to Embodiment 1 are arranged more regularly. That is because the detector ring 12 is manufactured by adjusting the position of each member that supports the scintillator 2 with reference to the position of the scintillator 2. The detector ring 12 has the detector unit 14. Here, the positions of the three scintillators 2 of the detector unit 14 are regular. Specifically, the scintillation counter crystals that form the detector unit 19 are regularly arranged over three scintillators 2 that constitute the detector array 14, since clearance Dx of each scintillator 2 corresponds to integral multiples of the arrangement pitch Dc of the scintillation counter crystals. In addition, the detector ring 12 is formed through annularly arranging of the detector units 19. The position of the detector unit 19 is also determined with reference to the scintillator 2. That is because the detector unit 19 is positioned with respect to the bottom plate 13 by contacting the alignment jig 30 placed inside the circular ring to the cover 25. As noted above, Embodiment 1 may arrange the scintillators 2 more regularly, which results in provision of radiation tomography apparatus having higher spatial resolution.

This invention is not limited to the foregoing embodiments, but may be modified as follows.

(1) In each of the foregoing embodiments, the scintillation counter crystal is composed of LYSO. Alternatively, the scintillation counter crystal may be composed of another materials, such as GSO ($Gd_2SiO_5$), may be used in this invention. According to this modification, a method of manufacturing a radiation detector may be provide that allows provision of a radiation detector of low price.

(2) In each of the foregoing embodiments, the scintillator 2 has four scintillation counter crystal layers. This invention is not limited to this embodiment. For instance, the scintillator formed of one scintillation counter crystal layer may be applied to this invention. Moreover, the scintillation counter crystal layer may be freely adjusted in number depending on applications of the radiation detector.

(3) The fluorescence detector in each of the foregoing embodiments is formed of the photomultiplier tube. This invention is not limited to this embodiment. A photodiode or an avalanche photodiode, etc. may be used instead of the photomultiplier tube.

(4) The detector ring in each of the foregoing embodiments is formed of the photomultiplier tube. This invention is not limited to this embodiment. The number of the detector units may be modified optionally in accordance with use of radiographic apparatus. Accordingly, the alignment jig may be modified in its rotational symmetry property.

INDUSTRIAL UTILITY

As described above, this invention is suitable for a method of manufacturing radiation tomography apparatus for use in medical fields.

The invention claimed is:

1. A method of manufacturing radiation tomography apparatus having an annular detector ring, the detector ring having detector arrays in a ring shape with each of radiation detectors arranged in a first direction in which a scintillator provided with scintillation counter crystal layers that is formed of scintillation counter crystals that convert radiation into fluorescence are arranged two-dimensionally in the first direction and a second direction as vertical and horizontal directions, a light guide that receives fluorescence, and a light detector that detects fluorescence are laminated in a height direction, comprising:

a preliminary arranging step of arranging a first radiation detector and a second radiation detector in the first direction and selects a spacer such that clearance in the first direction between a first scintillator provided in the first radiation detector and a second scintillator provided in the second radiation detector corresponds to integral multiples of an arrangement pitch of the scintillation counter crystal in the first direction;

a first spacer joining step of joining the spacer so as to cover a side surface of a first light detector provided in the first radiation detector that faces the first direction thereof;

a second spacer joining step of arranging the first radiation detector and the second radiation detector again in the first direction to align both radiation detectors in the second direction such that the first scintillator is same as the second scintillator in position in the second direction, and joining the spacer to a side surface of a second light detector provided in the second radiation detector to manufacture the detector array extending in the first direction; and a detector ring forming step of forming the detector ring by arranging the detector arrays annularly.

2. The method of manufacturing the radiation tomography apparatus according to claim 1, further comprising a shim placing step of placing a shim for adjusting an opposite angle of the first scintillator and the second scintillator between the one side surface of the second light detector and the spacer, subsequent to the first spacer joining step.

3. The method of manufacturing the radiation tomography apparatus according to claim 2, wherein, in the second spacer joining step, the shim is also joined to the one side surface of the second light detector and the spacer while the one side surface of the second light detector is joined to the spacer.

4. The method of manufacturing the radiation tomography apparatus according to claim 1, wherein the detector ring forming step comprises a detector unit manufacturing step of manufacturing a detector unit by fixing the radiation detector that constitutes the detector array on a support tool that extends in the first direction;

a cover attaching step of attaching a cover for covering an upper surface of the scintillators of the detector unit;

a detector unit placing step of placing the detector unit on a ring-shaped bottom plate in the first direction such that the scintillators are directed toward inside of the bottom plate, thereby forming a circular ring with the detector units being arranged in a ring shape;

an alignment jig placing step of placing a columnar alignment jig inside the circular ring having contact surfaces that face to each of the covers provided in the detector unit; and a detector unit fixing step of fixing the detector unit on the bottom plate by contacting the cover provided in the detector unit to the contact surface to determine a position of the detector unit with respect to the bottom plate.

5. The method of manufacturing the radiation tomography apparatus according to claim 4, wherein the alignment jig has a first mark that indicates a position of the detector unit whereas the cover has a second mark that indicates a position of the detector unit in the second direction, and the detector unit is determined with respect to the bottom plate with reference to the first mark and the second mark.

6. The method of manufacturing the radiation tomography apparatus according to claim 5, wherein
the first mark and the and second mark are linear marks.

7. The method of manufacturing the radiation tomography apparatus according to claim 1, wherein
Transparent material is provided between the scintillation counter crystals adjacent to each other.

8. The method of manufacturing the radiation tomography apparatus according to claim 2, wherein
Transparent material is provided between the scintillation counter crystals adjacent to each other.

9. The method of manufacturing the radiation tomography apparatus according to claim 3, wherein
Transparent material is provided between the scintillation counter crystals adjacent to each other.

10. The method of manufacturing the radiation tomography apparatus according to claim 3, wherein the detector ring forming step comprises
a detector unit manufacturing step of manufacturing a detector unit by fixing the radiation detector that constitutes the detector array on a support tool that extends in the first direction;
a cover attaching step of attaching a cover for covering an upper surface of the scintillators of the detector unit;
a detector unit placing step of placing the detector unit on a ring-shaped bottom plate in the first direction such that the scintillators are directed toward inside of the bottom plate, thereby forming a circular ring with the detector units being arranged in a ring shape;
an alignment jig placing step of placing a columnar alignment jig inside the circular ring having contact surfaces that face to each of the covers provided in the detector unit; and
a detector unit fixing step of fixing the detector unit on the bottom plate by contacting the cover provided in the detector unit to the contact surface to determine a position of the detector unit with respect to the bottom plate.

11. The method of manufacturing the radiation tomography apparatus according to claim 10, wherein
the alignment jig has a first mark that indicates a position of the detector unit whereas the cover has a second mark that indicates a position of the detector unit in the second direction, and
the detector unit is determined with respect to the bottom plate with reference to the first mark and the second mark.

12. The method of manufacturing the radiation tomography apparatus according to claim 4, wherein
Transparent material is provided between the scintillation counter crystals adjacent to each other.

13. The method of manufacturing the radiation tomography apparatus according to claim 10, wherein
Transparent material is provided between the scintillation counter crystals adjacent to each other.

14. The method of manufacturing the radiation tomography apparatus according to claim 5, wherein
Transparent material is provided between the scintillation counter crystals adjacent to each other.

15. The method of manufacturing the radiation tomography apparatus according to claim 2, wherein the detector ring forming step comprises
a detector unit manufacturing step of manufacturing a detector unit by fixing the radiation detector that constitutes the detector array on a support tool that extends in the first direction;
a cover attaching step of attaching a cover for covering an upper surface of the scintillators of the detector unit;
a detector unit placing step of placing the detector unit on a ring-shaped bottom plate in the first direction such that the scintillators are directed toward inside of the bottom plate, thereby forming a circular ring with the detector units being arranged in a ring shape;
an alignment jig placing step of placing a columnar alignment jig inside the circular ring having contact surfaces that face to each of the covers provided in the detector unit; and
a detector unit fixing step of fixing the detector unit on the bottom plate by contacting the cover provided in the detector unit to the contact surface to determine a position of the detector unit with respect to the bottom plate.

16. The method of manufacturing the radiation tomography apparatus according to claim 15, wherein
the alignment jig has a first mark that indicates a position of the detector unit whereas the cover has a second mark that indicates a position of the detector unit in the second direction, and
the detector unit is determined with respect to the bottom plate with reference to the first mark and the second mark.

17. The method of manufacturing the radiation tomography apparatus according to claim 16, wherein
Transparent material is provided between the scintillation counter crystals adjacent to each other.

18. The method of manufacturing the radiation tomography apparatus according to claim 16, wherein
the first mark and the and second mark are linear marks.

19. The method of manufacturing the radiation tomography apparatus according to claim 15, wherein
Transparent material is provided between the scintillation counter crystals adjacent to each other.

20. The method of manufacturing the radiation tomography apparatus according to claim 11, wherein
the first mark and the and second mark are linear marks.

* * * * *